(12) United States Patent
Pelligrini

(10) Patent No.: US 9,068,969 B2
(45) Date of Patent: Jun. 30, 2015

(54) CELL BASED METHODS AND SYSTEMS FOR THE IDENTIFICATION OF RNA REGULATORY SEQUENCES AND COMPOUNDS THAT MODULATE THEIR FUNCTIONS

(75) Inventors: Matthew C. Pelligrini, Bedminster, NJ (US); Christopher R. Trotta, legal representative, Somerset, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 1510 days.

(21) Appl. No.: 11/813,027

(22) PCT Filed: Dec. 27, 2005

(86) PCT No.: PCT/US2005/047156
§ 371 (c)(1),
(2), (4) Date: Aug. 7, 2008

(87) PCT Pub. No.: WO2006/071903
PCT Pub. Date: Jul. 6, 2006

(65) Prior Publication Data
US 2008/0318222 A1    Dec. 25, 2008

Related U.S. Application Data

(60) Provisional application No. 60/639,833, filed on Dec. 28, 2004.

(51) Int. Cl.
| | | |
|---|---|---|
| *C12Q 1/68* | (2006.01) | |
| *G01N 33/50* | (2006.01) | |
| *C12N 15/10* | (2006.01) | |
| *C07H 21/02* | (2006.01) | |
| *C07H 21/04* | (2006.01) | |

(52) U.S. Cl.
CPC .............. *G01N 33/5008* (2013.01); *C12Q 1/68* (2013.01); *C12N 15/1086* (2013.01)

(58) Field of Classification Search
None
See application file for complete search history.

(56) References Cited

U.S. PATENT DOCUMENTS

| 5,610,015 A * | 3/1997 | Wickens et al. .................. 435/6 |
| 6,291,637 B1 * | 9/2001 | Das et al. ...................... 530/300 |
| 2003/0208783 A1 * | 11/2003 | Hillen et al. ...................... 800/8 |
| 2004/0067540 A1 | 4/2004 | Lassota |

FOREIGN PATENT DOCUMENTS

WO    WO2004067728    8/2004

OTHER PUBLICATIONS

Xu et al. Effective small interfering RNAs and phosphorothioate antisense DNAs have different preferences for target sites in the luciferase mRNAs. Biochemical and Biophysical Research Communications, vol. 306, No. 3, pp. 712-717, Jul. 2003.*
Gale et al. Translational control of viral gene expression in eukaryotes. Microbiology and Molecular Biology Reviews, vol. 64, No. 2, pp. 239-280, Jun. 2000.*
Tallet-Lopez et al. Antisense oligonucleotides targeted to the domain IIId of the hepatitis C virus IRES compete with 40S ribosomal subunit binding and prevent in vitro translation. Nucleic Acids Research, vol. 31, No. 2, pp. 734-742, Jan. 2003.*
Schneider et al. Translation initiation and viral tricks. TRENDS in Biochemical Sciences, vol. 28, No. 3, pp. 130-136, Mar. 2003.*
Dasgupta et al. Targeting internal ribosome entry site (IRES)-mediated translation to block hepatitis C and other viruses. FEMS Microbiology Letters, vol. 234, pp. 189-199, May 2004.*
Pudi et al. Hepatitis C virus internal ribosome entry site-mediated translation is stimulated by specific interaction of independent regions of human La autoantigen. The Journal of Biological Chemistry, vol. 278, No. 14, pp. 12231-12240, Apr. 2003.*
Sandrock et al. Three-hybrid screens.: Inducible third-party systems. Methods in Molecular Biology, vol. 177, pp. 271-289, 2001.*
Zhivotovsky et al. "Current concepts in cell death" in Current Protocols in Cell Biology, Chapter 18: Unit 18.1, pp. 18.1.1-18.1.18, Aug. 2001.*
Strathdee et al.; Efficient Control of Tetracycline-Responsive Gene Expression From an Autoregulated Bi-directional Expression Vector. Gene., vol. 229, pp. 21-29, especially pp. 23-24 and 29, 1999.
Otero et al., A 250-nucleotide UA-rich Element in the 3' Untranslated Region of *Xenopus laevis* Vg1 mRNA Represses Translation both in vivo and in vitro. RNA, 2001, vol. 7, pp. 1753-1767, especially p. 1765.

* cited by examiner

*Primary Examiner* — Celine Qian
*Assistant Examiner* — Nancy J Leith
(74) *Attorney, Agent, or Firm* — Hoffmann & Baron, LLP

(57) ABSTRACT

The present invention is directed to methods of screening for a small molecule that modulates the ability of a RNA regulatory sequence to inhibit mRNA translation in a mammalian cell comprising incubating the mammalian cell expressing a reporter mRNA and the RNA regulatory sequence in the presence of the small molecule, wherein the RNA regulatory sequence is not attached to the reporter mRNA; and monitoring a reporter protein signal produced by the reporter mRNA, wherein a change in the signal of the reporter protein in the presence of the small molecule compared to the reporter protein signal in the absence of the small molecule indicates the small molecule modulates the ability of the RNA regulatory sequence to inhibit mRNA translation.

8 Claims, 5 Drawing Sheets

FIGURE 2A.

ggatccggcgacactccgccatgagtcactcccctgtgaggaactactgtcttcacgcagaaagcgtctagccatggcgttagtatgag tgtcgtacagcctccaggccccccccctcccgggagagccatagtggtctgcggaaccggtgagtacaccggaattaccggaaagact gggtcctttcttggataaacccactctatgtccggtcatttgggcgtgcccccgcaagactgctagccgagtagcgttgggttgcgaaag gccttgtggtactgcctgatagggtgcttgcgagtgccccgggaggtctcgtagaccgtgcatcatgagcacgaatcctggatcc (SEQ ID NO: 1)

T7: T7 promoter sequence

ORF: open reading frame of firefly luciferase

A50: polyA tail

```
                        SEQUENCE LISTING

<160> NUMBER OF SEQ ID NOS: 47

<210> SEQ ID NO 1
<211> LENGTH: 339
<212> TYPE: DNA
<213> ORGANISM: Hepatitis C virus
<220> FEATURE:
<221> NAME/KEY: misc_feature
<223> OTHER INFORMATION: nucleotides 18 to 356 of IRES coding sequence

<400> SEQUENCE: 1
ggcgacactc cgccatgagt cactccctg tgaggaacta ctgtcttcac gcagaaagcg        60
tctagccatg gcgttagtat gagtgtcgta cagcctccag gccccccct cccgggagag       120 ccatagtggt ctgcggaacc ggtgagtaca ccggaattac cggaaagact gggtcctttc      180
ttggataaac ccactctatg tccggtcatt tgggcgtgcc cccgcaagac tgctagccga      240
gtagcgttgg gttgcgaaag gccttgtggt actgcctgat agggtgcttg cgagtgcccc      300
gggaggtctc gtagaccgtg catcatgagc acgaatcct                             339

<210> SEQ ID NO 2
<211> LENGTH: 33
<212> TYPE: RNA
<213> ORGANISM: Hepatitis C virus
<220> FEATURE:
<221> NAME/KEY: misc_feature
<223> OTHER INFORMATION: domain IIb of HCV-UTR RNA

<400> SEQUENCE: 2
ggcagaaagc gucuagccau ggcguuagua uga                                    33

<210> SEQ ID NO 3
<211> LENGTH: 50
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 3
taatacgact cactataggc agaaagcgtc tagccatggc gttagtatga                  50

<210> SEQ ID NO 4
<211> LENGTH: 50
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 4
tcatactaac gccatggcta gacgctttct gcctatagtg agtcgtatta                  50
```

```
<210> SEQ ID NO 5
<211> LENGTH: 26
<212> TYPE: RNA
<213> ORGANISM: Hepatitis C virus
<220> FEATURE:
<221> NAME/KEY: misc_feature
<223> OTHER INFORMATION: domain IV of HCV-UTR RNA

<400> SEQUENCE: 5
ggaccgugca ucaugagcac gaaucc                                    26

<210> SEQ ID NO 6
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 6
taatacgact cactatagga ccgtgcatca tgagcacgaa tcc                  43

<210> SEQ ID NO 7
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 7
ggattcgtgc tcatgatgca cggtcctata gtgagtcgta tta                  43

<210> SEQ ID NO 8
<211> LENGTH: 48
<212> TYPE: RNA
<213> ORGANISM: Hepatitis C virus
<220> FEATURE:
<221> NAME/KEY: misc_feature
<223> OTHER INFORMATION: domain IIIb of HCV-UTR RNA

<400> SEQUENCE: 8
ggccggaaag acugguccu uucuuggaua aacccacucu auguccgg              48

<210> SEQ ID NO 9
<211> LENGTH: 65
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 9
taatacgact cactataggc cggaaagact gggtcctttc ttggataaac ccactctatg   60
tccgg                                                             65

<210> SEQ ID NO 10
<211> LENGTH: 65
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<223> OTHER INFORMATION: oligonucleotide

<400> SEQUENCE: 10
ccggacatag agtgggttta tccaagaaag gacccagtct ttccggccta tagtgagtcg      60
tatta                                                                 65

<210> SEQ ID NO 11
<211> LENGTH: 49
<212> TYPE: RNA
<213> ORGANISM: Hepatitis C virus
<220> FEATURE:
<221> NAME/KEY: misc_feature
<223> OTHER INFORMATION: domain IIa of HCV-UTR RNA

<400> SEQUENCE: 11
ggccugugag gaacuacugu cuucacuucg gugucguaca gccuccagg                 49

<210> SEQ ID NO 12
<211> LENGTH: 66
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 12
taatacgact cactataggc ctgtgaggaa ctactgtctt cacttcggtg tcgtacagcc     60
tccagg                                                                66

<210> SEQ ID NO 13
<211> LENGTH: 66
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: oligonucleotide

<400> SEQUENCE: 13
cctggaggct gtacgacacc gaagtgaaga cagtagttcc tcacaggcct atagtgagtc     60
gtatta                                                                66

<210> SEQ ID NO 14
<211> LENGTH: 103
<212> TYPE: RNA
<213> ORGANISM: Hepatitis C virus
<220> FEATURE:
<221> NAME/KEY: misc_feature
<223> OTHER INFORMATION: domain IIab of HCV-UTR-RNA

<400> SEQUENCE: 14
ggcgacacuc cgccaugagu cacuccccug ugaggaacua cugucuucac gcagaaagcg     60
ucuagccaug gcguuaguau gagugucgua cagccuccag gcc                      103

<210> SEQ ID NO 15
<211> LENGTH: 40
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<223> OTHER INFORMATION: PCR primer

<400> SEQUENCE: 15
taatacgact cactataggc gacactccgc catgagtcac                           40

<210> SEQ ID NO 16
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 16
ggcctggagg ctgtacgaca ctcatac                                         27

<210> SEQ ID NO 17
<211> LENGTH: 114
<212> TYPE: RNA
<213> ORGANISM: Hepatitis C virus
<220> FEATURE:
<221> NAME/KEY: misc_feature
<223> OTHER INFORMATION: domain III abc of HCV-UTR RNA

<400> SEQUENCE: 17
gguagugguc ugcggaaccg gugaguacac cggaauuacc ggaaagacug gguccuuucu     60
uggauaaacc cacucuaugu ccggucauuu gggcgugccc ccgcaagacu gcua          114

<210> SEQ ID NO 18
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 18
taatacgact cactataggt agtggtctgc ggaaccgg                             38

<210> SEQ ID NO 19
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 19
tagcagtctt gcgggggcac g                                               21

<210> SEQ ID NO 20
<211> LENGTH: 159
<212> TYPE: RNA
<213> ORGANISM: Hepatitis C virus
<220> FEATURE:
<221> NAME/KEY: misc_feature
<223> OTHER INFORMATION: domain III abcd of HCV-UTR RNA
```

```
<400> SEQUENCE: 20
ggagagccau aguggucugc ggaaccggug aguacaccgg aauuaccgga aagacugggu      60 ccuucuugg auaaacccac ucuaugccg gucauuggg cgugccccg caagacugcu         120 agccgaguag cguuggguug cgaaaggccu uguggguacu                            159

<210> SEQ ID NO 21
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 21
taatacgact cactatagga gagccatagt ggtctgcgg                              39

<210> SEQ ID NO 22
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 22
agtaccacaa ggcctttcgc                                                   20

<210> SEQ ID NO 23
<211> LENGTH: 86
<212> TYPE: RNA
<213> ORGANISM: Hepatitis C virus
<220> FEATURE:
<221> NAME/KEY: misc_feature
<223> OTHER INFORMATION: domain III def of HCV-UTR RNA

<400> SEQUENCE: 23
ggcugcuagc cgaguagcgu ugggguugcga aaggccuugu gguacugccu gauagggugc      60
uugcgagugc cccgggaggu cucgua                                            86

<210> SEQ ID NO 24
<211> LENGTH: 36
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 24
taatacgact cactataggc tgctagccga gtagcg                                 36

<210> SEQ ID NO 25
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer
```

```
<400> SEQUENCE: 25
tacgagacct cccggggcac                                                      20

<210> SEQ ID NO 26
<211> LENGTH: 214
<212> TYPE: RNA
<213> ORGANISM: Hepatitis C virus
<220> FEATURE:
<221> NAME/KEY: misc_feature
<223> OTHER INFORMATION: domain III of HCV-UTR RNA

<400> SEQUENCE: 26
ggcccccccc ucccgggaga gccauagugg ucugcggaac cggugaguac accggaauua          60
ccggaaagac ugguccuuuu cuuggauaaa cccacucuau guccggucau uugggcgugc         120
ccccgcaaga cugcuagccg aguagcguug gguugcgaaa ggccuugugg uacugccuga         180
uagggugcuu gcgagugccc cgggaggucu cgua                                      214

<210> SEQ ID NO 27
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 27
taatacgact cactataggc ccccccctcc cgggagagcc                                 40

<210> SEQ ID NO 28
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 28
tacgagacct cccggggcac                                                      20

<210> SEQ ID NO 29
<211> LENGTH: 210
<212> TYPE: RNA
<213> ORGANISM: Hepatitis C virus
<220> FEATURE:
<221> NAME/KEY: misc_feature
<223> OTHER INFORMATION: domain II-IIIb of HCV-UTR RNA

<400> SEQUENCE: 29
ggcgacacuc cgccaugagu cacuccccug ugaggaacua cugucuucac gcagaaagcg          60
ucuagccaug gcguuaguau gagugucgua cagccuccag gccccccccu cccgggagag         120
ccauaguggu cugcggaacc ggugaguaca ccggaauuac cggaaagacu gguccuuuc          180 uuggauaaac ccacucuaug uccggucauu                                           210

<210> SEQ ID NO 30
<211> LENGTH: 40
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<223> OTHER INFORMATION: PCR primer

<400> SEQUENCE: 30
taatacgact cactataggc gacactccgc catgagtcac                             40

<210> SEQ ID NO 31
<211> LENGTH: 29
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 31
ggaatgaccg gacatagagt gggtttatc                                        29

<210> SEQ ID NO 32
<211> LENGTH: 235
<212> TYPE: RNA
<213> ORGANISM: Hepatitis C virus
<220> FEATURE:
<221> NAME/KEY: misc_feature
<223> OTHER INFORMATION: domain II-IIIabc of HCV-UTR RNA

<400> SEQUENCE: 32
ggcgacacuc cgccaugagu cacuccccug ugaggaacua cugucuucac gcagaaagcg      60
ucuagccaug gcguuaguau gagugucgua cagccuccag gccccccccu cccgggagag     120
ccauaguggu cugcggaacc ggugaguaca ccggaauuac cggaaagacu gguccuuuc      180 uuggauaaac ccacucuaug uccggucauu ugggcgugcc ccgcaagac ugcua           235

<210> SEQ ID NO 33
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 33
taatacgact cactataggc gacactccgc catgagtcac                             40

<210> SEQ ID NO 34
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 34
tagcagtctt gcgggggcac g                                                21

<210> SEQ ID NO 35
<211> LENGTH: 290
<212> TYPE: RNA
<213> ORGANISM: Hepatitis C virus
```

<220> FEATURE:
<221> NAME/KEY: misc_feature
<223> OTHER INFORMATION: domain II-III abcd of HCV-RNA UTR

<400> SEQUENCE: 35

| | | | | | |
|---|---|---|---|---|---|
| uaauacgacu | cacuauaggc | gacacuccgc | caugagucac | uccccuguga | ggaacuacug | 60 |
| ucuucacgca | gaaagcgucu | agccauggcg | uuaguaugag | ugucguacag | ccuccaggcc | 120 |
| cccccuccc | gggagagcca | uaguggucug | cggaaccggu | gaguacaccg | gaauuaccgg | 180 |
| aaagacuggg | uccuuucuug | gauaaaccca | cucuaugucc | ggucauuugg | gcgugccccc | 240 |
| gcaagacugc | uagccgagua | gcguuggguu | gcgaaaggcc | uuguggguacu | | 290 |

<210> SEQ ID NO 36
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 36
taatacgact cactataggc gacactccgc catgagtcac                                  40

<210> SEQ ID NO 37
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 37
agtaccacaa ggcctttcgc                                                        20

<210> SEQ ID NO 38
<211> LENGTH: 289
<212> TYPE: RNA
<213> ORGANISM: Hepatitis C virus
<220> FEATURE:
<221> NAME/KEY: misc_feature
<223> OTHER INFORMATION: domain II-III of HCV-UTR RNA

<400> SEQUENCE: 38

| | | | | | |
|---|---|---|---|---|---|
| ggccugugag | gaacuacugu | cuucacgcag | aaagcgucua | gccauggcgu | uaguaugagu | 60 |
| gucguacagc | cuccaggccc | cccccucccg | ggagagccau | aguggucugc | ggaaccggug | 120 |
| aguacaccgg | aauuaccgga | aagacugggu | ccuuucuugg | auaaacccac | ucuaugccg | 180 |
| gucauuuggg | cgugcccccg | caagacugcu | agccgaguag | cguuggguug | cgaaaggccu | 240 |
| ugugguacug | ccugauaggg | ugcuugcgag | ugccccggga | ggucucgua | | 289 |

<210> SEQ ID NO 39
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 39
taatacgact cactataggc gacactccgc catgagtcac        40

<210> SEQ ID NO 40
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 40
tacgagacct cccgggcac        20

<210> SEQ ID NO 41
<211> LENGTH: 239
<212> TYPE: RNA
<213> ORGANISM: Hepatitis C virus
<220> FEATURE:
<221> NAME/KEY: misc_feature
<223> OTHER INFORMATION: domain III/IV of HCV-UTR RNA

<400> SEQUENCE: 41 ggccccccccc ucccgggaga gccauagugg ucugcggaac cggugaguac accggaauua        60
ccggaaagac uggguccuuu cuuggauaaa cccacucuau guccggucau uugggcgugc       120
ccccgcaaga cugcuagccg aguagcguug gguugcgaaa ggccuugugg uacugccuga       180 uaggguugcuu gcgagugccc cgggaggucu cguagaccgu gcaucaugag cacgaaucc       239

<210> SEQ ID NO 42
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 42
taatacgact cactataggc ccccccctcc cgggagagcc        40

<210> SEQ ID NO 43
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 43
ggattcgtgc tcatgatgca cggtcctata gtgagtcgta tta        43

<210> SEQ ID NO 44
<211> LENGTH: 338
<212> TYPE: RNA
<213> ORGANISM: Hepatitis C virus
<220> FEATURE:
<221> NAME/KEY: misc_feature
<223> OTHER INFORMATION: domain II/III/IV of HCV-UTR RNA

```
<400> SEQUENCE: 44
ggcgacacuc cgccaugagu cacuccccug ugaggaacua cugucuucac gcagaaagcg    60
ucuagccaug gcguuaguau gagugucgua cagccuccag gccccccccu cccgggagag   120
ccauaguggu cugcggaacc ggugaguaca ccggaauuac cggaaagacu ggguccuuuc   180
uuggauaaac ccacucuaug uccggucauu ugggcgugcc cccgcaagac ugcuagccga   240
guagcguugg guugcgaaag gccuuguggu acugccugau agggugcuug cgagugcccc   300
gggaggucuc guagaccgug caucaugagc acgaaucc                          338

<210> SEQ ID NO 45
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 45
taatacgact cactataggc gactctccgc catgagtcac                          40

<210> SEQ ID NO 46
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 46
ggattcgtgc tcatgatgca cggtcctata gtgagtcgta tta                      43

<210> SEQ ID NO 47
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: PCR primer

<400> SEQUENCE: 47
taatacgact cactatagg                                                 19
```

CELL BASED METHODS AND SYSTEMS FOR THE IDENTIFICATION OF RNA REGULATORY SEQUENCES AND COMPOUNDS THAT MODULATE THEIR FUNCTIONS

CROSS-REFERENCE TO RELATED APPLICATIONS

This application is a national stage filing under 35 U.S.C. 371 of International Application No. PCT/US2005/047156, filed Dec. 27, 2005, which claims priority to U.S. Provisional Application No. 60/639,833, filed Dec. 28, 2004.

FIELD OF THE INVENTION

The present invention relates to the identification of RNA regulatory sequences and compounds that modulate gene expression at the post-transcriptional level. More specifically, the invention relates to the screening for RNA sequences able to inhibit the translation of a reporter mRNA and for compounds able to reverse the inhibition of translation.

BACKGROUND OF THE INVENTION

Gene expression is controlled at many different steps in the pathway from DNA to RNA to protein. Because aberrant gene expression can lead to a disease state, such as cancer, genes must be tightly regulated to ensure they are expressed at the correct time, place and level. While most efforts have been aimed at understanding transcriptional regulation of gene expression (i.e., DNA to RNA) and its contribution to disease, regulation at other levels such as mRNA translation (i.e., RNA to protein) or RNA stability remains less well understood. It is only recently that research into post-transcriptional mechanisms of gene expression has uncovered that regulation of mRNA translation, or translational control, is a critical checkpoint in gene expression linked to a variety of disease processes (Cazzola and Skoda, Blood 95: 3280-3288, 2000).

Translational control occurs in virtually all cell types and species where it contributes to such diverse processes as cell-cycle control, learning and plasticity in neurons, and red blood cell differentiation, among many others. Because translational control enables a cell to increase the concentration of a protein very rapidly, this mechanism of control is especially suited for the regulation of genes that are involved in cell proliferation and damage control. Regulation of gene expression at the level of mRNA translation is also particularly important in cellular responses to development or environmental stimuli—such as nutrient levels, cytokines, hormones, and temperature shifts, as well as environmental stresses—such as hypoxia, hypocalcemia, viral infection, and tissue injury. Translational control can be either global, affecting all the mRNAs in a cell, or specific to a single or subset of mRNAs.

The typical mRNA contains a 5' cap, a 5' untranslated region upstream of a start codon (5' UTR), an open reading frame, also referred to as coding sequence, that encodes a functional protein, a 3' untranslated region (3' UTR) downstream of the termination codon, and a poly(A) tail. The key mediators of translational control are typically found in the 5' and 3' untranslated regions of mRNA transcripts, although the possibility of regulatory sequences mapping even to the coding sequence itself cannot be excluded. Much like the linear array of amino acids in proteins, these single-stranded regions of RNA can fold into complex three-dimensional structures consisting of local motifs such as hairpins, stem-loops, bulges, pseudoknots, guanosine quartets, and turns (for reviews see Moore, Ann. Rev. Biochem. 68:287-300, 1999; Gallego and Varani, Acc. Chem. Res. 34:836-843, 2001). Through interactions with regulatory proteins, such structures can be critical to the activity of the nucleic acid and dramatically affect the regulation of mRNA translation.

Because the sequences of an mRNA often contain critical regulatory elements which influence translational efficiency, compounds that are able to modulate the effect of the regulatory RNA sequence would be highly useful in therapeutic applications that seek to up- or downregulate the expression of a gene. Current approaches for blocking the function of target nucleic acids include the use of duplex-forming antisense oligonucleotides (Bennett and Cowsert, Biochem. Biophys. Acta 1489 (1): 19-30, 1999), peptide nucleic acids ("PNA"; Gambari, Curr. Pharm. Des. 7 (17): 1839-1862, 2001; Nielsen, Curr. Opin. Struct. Biol. 9 (3): 353-357, 1999; Nielsen, Curr. Opin. Biotechol. 10 (1): 71-75, 1999) and locked nucleic acid ("LNA"; Braasch & Corey, Chem. Biol. 8 (1): 1-7, 2001; Arzumanov et al., Biochemistry 40 (48): 14645-14654, 2001), which bind to nucleic acids via Watson-Crick base-pairing. However, the dependence on the native three-dimensional structural motifs of single-stranded stretches for regulatory functions can preclude the use of general, simple-to-use, sequence-specific recognition rules to design complementary agents that bind to these motifs.

Previous efforts to identify compounds or agents that recognize regulatory RNA elements have primarily focused on characterizing regulatory proteins that bind to a particular regulatory mRNA sequence, and on elucidating molecular mechanisms by which the protein-mRNA complex exerts its effect on translational control before identifying potential modulators. A major disadvantage of such approaches is the lengthy and laborious procedure required to isolate and identify proteins that bind to specific mRNA regulatory sequences. In addition to isolating the proteins that bind to regulatory mRNA sequences, these approaches have also either required the labeling of particular proteins or RNAs or depended on the linkage of the RNA regulatory sequence to a reporter, or a combination thereof. All these are time-consuming and laborious procedures that require a series of complex laboratory manipulations and often deliver false positive results. There is thus a need for a simplified method to identify modulators of translational control of gene expression that eliminates the requirement for a series of intermediate steps and yields a direct functional readout.

SUMMARY OF THE INVENTION

The present invention provides an in vivo method of screening for and/or identifying an RNA regulatory element. The method comprises culturing cells including: a translation system; an RNA test sequence; and a reporter mRNA under suitable conditions for translation of the reporter mRNA; wherein the RNA test sequence is not linked to the reporter mRNA. The method further includes measuring the effect of the RNA test sequence on the translation of the reporter mRNA, wherein a test sequence that modifies the translation of the reporter mRNA includes an RNA regulatory element.

A test sequence which inhibits translation of the reporter mRNA, as compared to in the absence of the test sequence, can include an RNA regulatory element. Furthermore, a test sequence which increases the translation of the reporter mRNA, as compared to in the absence of the test sequence, can include an RNA regulatory element.

The present invention further provides an in vivo method of screening for and/or identifying at least one test compound, which modulates the ability of an RNA sequence to regulate mRNA translation in a cell. The method comprises culturing cells including: a translation system; a reporter mRNA; and an RNA regulatory sequence in the presence of at least one test compound, whose ability to affect the interaction between the RNA regulatory sequence and at least one component of the translation system is sought to be determined, wherein the RNA regulatory sequence is not attached to the reporter mRNA. The method further includes monitoring for the effect of the at least one test compound on the interaction between the RNA regulatory sequence and component(s) of the translation machinery, wherein a compound that modifies this interaction is a drug candidate.

For example, the RNA regulatory sequence can inhibit the translation of the reporter mRNA. In this instance, the method can be used to assess whether a particular test compound(s) reverses the inhibition, as measured by an increase in translation of the reporter mRNA.

Another aspect of the invention relates to in vivo translation systems. One system provided herein comprises cells including a translation system; an RNA regulatory sequence; and a reporter mRNA; wherein the RNA regulatory sequence modifies the translation of the reporter mRNA and is not attached to the reporter mRNA. The cell-based system can be used in a screening method according to the present invention for identifying a test compound that modulates the ability of the RNA regulatory sequence to regulate translation of the reporter mRNA. In particular, a test compound can be introduced into the system and the extent of modulation of translation of the reporter mRNA can be determined.

The present invention also provides an in vivo translation system that comprises cells including a translation system; an RNA regulatory sequence; and a reporter mRNA; wherein the RNA regulatory sequence inhibits translation of the reporter mRNA and is not attached to the reporter mRNA. This system can be used in a screening method provided by the present invention for identifying a test compound which is capable of reversing the inhibition of translation. In particular, a test compound can be introduced into the cell-based system and the extent of reverse inhibition of translation of the reporter mRNA can be assessed.

Also provided by the invention is a test compound identified by a screening method of the present invention and a use therefore. For example, a test compound identified in a screening method of the present invention can be used in the manufacture of a medicine for modulating the expression of a gene including the RNA sequence. For example, the RNA sequence can be harbored within a gene involved in pathogenesis and/or pathophysiology. The expression of the gene may be aberrant in a disease state or may cause the survival and/or progression of a pathogenic organism.

DETAILED DESCRIPTION OF THE INVENTION

Figure 1A:
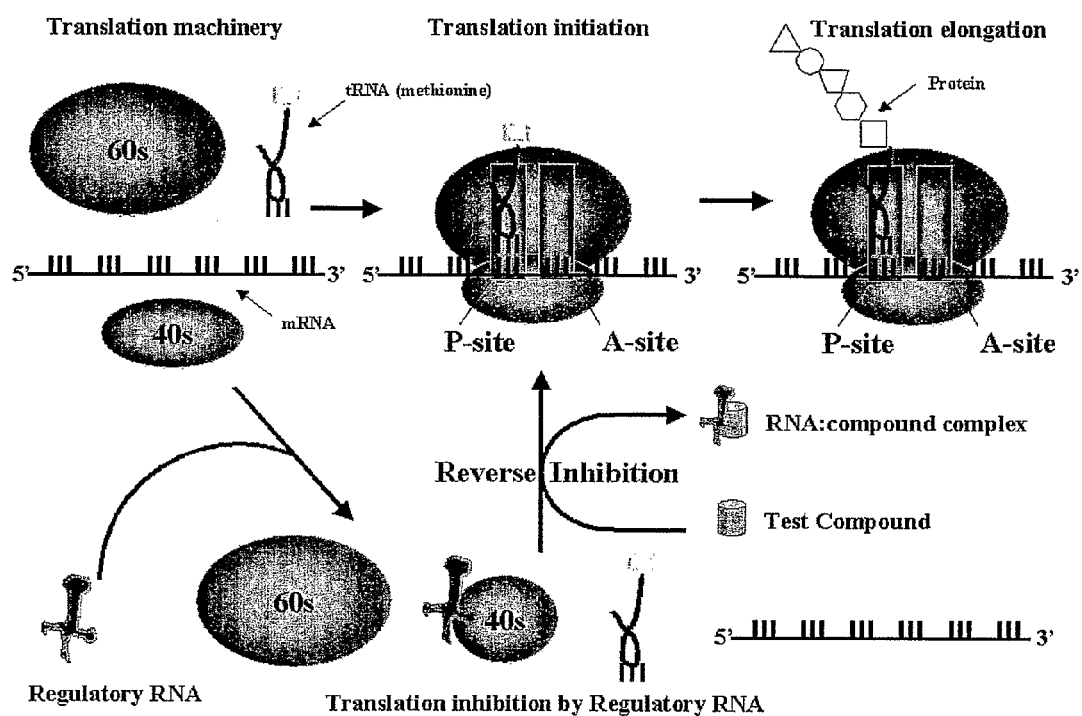
FIG. 1. (A) This figure shows the proposed mechanism of reverse inhibition of translation. The translation initiation process is a key step in the regulation of gene expression. RNA elements that mediate this regulation (regulatory RNA), when added exogenously to a translation system, can interact with any number of a large array of general translation components, such as the 40S ribosomal subunit (40S sphere), and inhibit gene expression. Test compounds (cylinder) that interact with the RNA regulatory element can reverse the inhibition of gene expression and modulate the expression of genes that harbor the regulatory RNA element. (B) This figure represents the proposed mechanism of reverse inhibition as an enzymatic reaction whose components are in thermodynamic equilibrium. In the absence of inhibitory RNA (I, inhibitor), the ribosome (E, enzyme) translates the mRNA (S, substrate) to generate the reporter enzyme (P, product). In the presence of I, E is sequestered and P formation is inhibited. However, the addition of a test compound (C, compound) that prevents the interaction between E and I allows free E to translate S for the production of P. Translation of S by E in the presence of C is herein referred to as Reverse Inhibition.

Various publications or patents are referred to in parentheses throughout this application to describe the state of the art to which the invention pertains. Each of these publications or patents is incorporated by reference herein.

The present invention relates to cell-based methods for screening and identifying RNA regulatory sequences and test compounds that modulate the expression of genes at post-transcriptional events. The terms "RNA regulatory element", "RNA regulatory sequence" or "RNA element" are used herein along with "UTR" and "UTR regulatory element," to denote those RNA sequences—both RNA only and/or protein-RNA complexes—that influence or regulate the translation machinery, be it positively by upregulating translation efficiency, or negatively by downregulating or inhibiting translation, regardless of where in the transcript they are located, i.e. in untranslated regions or in the coding sequence.

These RNA regulatory elements, when introduced exogenously to either a cell-free in vitro translation system containing reporter mRNA and cytoplasmic extract, or a cell-based translation system containing reporter mRNA, can act as antagonists of gene expression through direct competition for essential components of the general translational machinery, or through recruitment of regulatory proteins that interact with essential components of the general translation machinery.

In vitro methods were previously described by the present inventors in copending, commonly assigned International Application No. PCT/US2004/000423, filed Jan. 9, 2004, the entire contents of which are incorporated herein by reference. The present invention is directed to in vivo methods and systems for identifying RNA regulatory sequences and compounds that modulate gene expression at the post-transcriptional level.

Significantly, the ability of the RNA regulatory elements to inhibit the translation of the reporter mRNA when introduced exogenously to a translation system does not depend on whether the endogenous RNA regulatory element functions to decrease or increase translation of a corresponding coding sequence. Thus, the present invention allows the identification of both positive and negative RNA regulatory elements, as well as compounds that modulate the effects of both positive and negative RNA regulatory elements on the translational machinery.

Thus in a first aspect, the present invention allows for the speedy identification of novel RNA regulatory elements involved in translational control. By the systems and methods of the invention, any RNA test sequence of interest, or a fragment thereof, can be quickly and conveniently assayed for its ability to inhibit translation of a reporter mRNA.

For example, in one embodiment, a suitable test sequence corresponds to a sequence from the 5' UTR or 3' UTR of an mRNA of a target gene of interest. In another embodiment, a suitable test sequence corresponds to a sequence from the coding region of an mRNA of a target gene of interest. In a further embodiment, the test sequence is from an mRNA of a gene involved in pathogenesis and/or pathophysiology, as will be described in further detail below. For example, the RNA test sequence can be included within an mRNA of a gene selected from, but not limited to, the following: oncogenes, tumor suppressor genes, viral genes, genes coding for cytokines, genes coding for virokines and combinations thereof.

The present invention provides a method for screening for and/or identifying an RNA regulatory element. The method comprises culturing cells including: a translation system; an RNA test sequence; and a reporter mRNA under suitable conditions for translation of the reporter mRNA, wherein the RNA test sequence is not attached to the reporter mRNA. By the terms "not attached," "not linked" and the like it is meant that the RNA test sequence/RNA regulatory sequence and the reporter mRNA are not chemically attached to each other— neither directly nor indirectly (e.g., through a linker molecule). The method further involves measuring the effect of the test sequence on the translation of the reporter mRNA, wherein a test sequence that modifies the translation of the reporter mRNA includes an RNA regulatory element.

In one embodiment, the cells employed contain a genomic copy(s) of the reporter mRNA under the control of a constitutively active promoter sequence for expression of the reporter mRNA. In another embodiment, the cells contain an exogenously added DNA copy of the reporter mRNA, the reporter DNA being under the control of a constitutively active promoter sequence for expression of the reporter mRNA. For example, a DNA copy of the reporter mRNA can be transfected into the cells. In a further embodiment, the reporter mRNA is transfected into the cells. For example, methods are well known for efficiently transfecting eukaryotic cells with RNA.

In yet another embodiment, the cells contain an exogenously added DNA copy of the RNA test sequence. For example, a DNA copy of the test sequence can be transfected into the cells. In still yet another embodiment, the RNA test sequence is transfected into the cells.

In a preferred embodiment, the culturing step includes preincubating the translation system with the test sequence; and then combining the preincubated translation system with the reporter RNA. In another embodiment, the culturing step includes preincubating the translation system with the reporter mRNA; and subsequently combining the preincubated translation system with the test sequence.

The monitoring step can include monitoring for cell viability in the presence of the test sequence and comparing it to the cell viability in the absence of the test sequence. For example, the delivery of the RNA test sequence into the cells can significantly reduce their viability by down-regulating or inhibiting translation.

Cell viability assays are well known. For example, the Cell Titer-Blue™ Cell Viability Assay (Promega Corporation) provides a homogeneous, fluorescent method for monitoring cell viability. The assay is based on the ability of living cells to convert a redox dye (resazurin) into a fluorescent end product (resorufin). Non-viable cells rapidly lose their metabolic capacity and thus do not generate a fluorescent signal. The procedure involves addition of a reagent directly to cells cultured in serum-supplemented medium. After an incubation step, data are recorded using, for example, a plate-reading fluorometer or spectrophotometer.

Alternatively, the monitoring step can include detecting a signal resulting from translation of the reporter mRNA in the presence of the test sequence and comparing it to the signal resulting from translation of the reporter mRNA in the absence of the test sequence. For example, depending on the reporter, the signal can be selected from the following: enzymatic activity, fluorescence, bioluminescence and combinations thereof. In one desired embodiment, the measuring step includes detecting enzymatic activity resulting from gene expression of the reporter mRNA, as compared to in the absence of the RNA test sequence.

The reporter mRNA can correspond to the coding sequence for any number of known reporters in the art. For example, the reporter mRNA can correspond to the coding sequence for at least one of the following: firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, secreted alkaline phosphatase, combinations, derivatives and fragments thereof. The cells employed in the systems and methods of the present invention can contain a genomic copy(s) of a reporter mRNA under the control of a constitutively active promoter sequence. Alternatively, a reporter mRNA or a DNA copy thereof can be transfected into the cells.

A test sequence which inhibits the translation of the reporter mRNA, as compared to in the absence of the test sequence, can include an RNA regulatory element. Alternatively, a test sequence which increases the translation of the reporter mRNA, as compared to in the absence of the test sequence, can include an RNA regulatory element.

The cells employed in the systems and methods of the present invention can be selected from the following: human cells, yeast cells, amphibian cells, mouse cells, rat cells, hamster cells, rabbit cells, and bacterial cells. For example, the cells can be selected from the following: Chinese hamster ovary cells, Xenopus oocytes and reticulocytes.

In a further aspect, the instant invention allows for the identification of compounds or agents that modulate the regulatory activity of an RNA regulatory sequence of interest, as measured by a difference, such as an increase, in translation of the reporter mRNA, as compared to in the absence of the test compound. In particular, the invention provides an in vivo method of screening for and/or identifying at least one test compound which modulates the ability of an RNA sequence to regulate mRNA translation in a cell. The method comprises culturing cells including: (i) a translation system; (ii) the reporter mRNA; and (iii) an RNA regulatory sequence in the presence of at least one test compound, wherein the RNA regulatory sequence is not attached to the reporter mRNA. The test compound is one whose ability to affect the interaction between the RNA regulatory sequence and at least one component of the translation system is sought to be determined. The in vivo method also involves the step of monitoring for the effect of the at least one test compound on this interaction, wherein a compound that modifies the interaction is a drug candidate. The RNA regulatory sequence can be one identified by a method of the present invention. Alternatively, the RNA regulatory sequence can be a known RNA regulatory sequence.

The monitoring step can include monitoring for the presence of a signal resulting from translation of the reporter mRNA in the presence of the test compound, and comparing it to the signal resulting from translation of the reporter mRNA in the absence of the test compound. Alternatively, the monitoring step can include monitoring for cell viability in the presence of the test compound, and comparing it to the cell viability in the absence of the test compound. Suitable test compounds can be selected from, but are not limited to, the following: nucleic acids, peptides, peptide analogs, polypeptides, proteins, organic molecules and combinations thereof.

In one embodiment of the methods to screen test compounds, the step of culturing cells includes preincubating a cell-based translation system containing reporter mRNA with the test compound and introducing the RNA regulatory sequence into the preincubated system. Translational modification of a constitutively expressed reporter mRNA can be assessed when the RNA regulatory sequence is introduced into the contacted system.

An RNA sequence which includes an RNA regulatory element and influences and/or regulates translation of the reporter mRNA, as compared to in the absence of the RNA sequence, can be employed to screen for test compounds which can modulate this regulatory activity. The RNA sequence employed can include an RNA regulatory element identified by a method of the present invention, or can include an already known RNA regulatory element.

The RNA regulatory sequence can be introduced via exogenous addition of the RNA regulatory sequence or a DNA copy thereof. Alternatively, the RNA regulatory sequence can be introduced via inducible transcription. For example, the cells can contain a genomic copy of the regulatory RNA sequence, the genomic copy being under the control of an inducibly active promoter sequence.

The screening methods of the present invention can include the step of inducing the expression of the RNA regulatory sequence with a chemical inducer. In one aspect, the inducing step can include adding to the cells an inducer selected from, but not limited to, the following: tetracycline, deoxycycline, copper, a hormone or a combination of these.

For example, a genomic copy of a regulatory RNA sequence can be under the control of an inducible promoter, wherein the promoter is always inactivated until tetracycline is added. The more tetracycline added, the greater the amount of expression of the RNA regulatory sequence. In another example, a genomic copy of a regulatory sequence is under the control of a copper-inducible promoter, wherein the promoter is always inactivated until copper is added. The more copper added, the greater the amount of expression of the RNA regulatory sequence.

In any event, a test compound(s) can be screened by culturing cells including a translation system; an RNA regulatory sequence; and the reporter mRNA; and the at least one test compound, wherein the RNA sequence modifies translation of the reporter mRNA. The ability of the test compound to modify the function of the RNA regulatory sequence is monitored.

In one embodiment, the method assesses whether a test compound(s) inhibits the interaction between the RNA sequence and one or more components in the cell-based translation system. For example, the RNA sequence can increase or, alternatively, decrease the translation of the reporter mRNA by interacting with one or more components of the translation machinery, and a test compound may influence and/or modify this interaction.

The RNA sequence employed in the screen for target compounds may inhibit the translation of the reporter mRNA. In this instance, the method can be used to assess whether or not a test compound reverses the inhibition, as measured by an increase in translation of the reporter mRNA. This is illustrated in FIG. 1A, a description for which is in the Brief Description of the Drawings.

Test compounds that inhibit the interaction between the exogenously added RNA regulatory elements and one or more components of the general translational machinery relieve the antagonistic effect of the RNA regulatory elements on the translation of the reporter mRNA and cause an increase in gene expression, i.e., translation of the reporter mRNA.

In one embodiment, a test compound which increases the translation of the reporter mRNA when present, as compared to in its absence, is a reverse inhibitor. This increase in translation can be observed by monitoring for an increase in the reporter signal in presence of the test compound, as compared to in its absence.

In another embodiment, a test compound which decreases cell death when present, as compared to in its absence, is a reverse inhibitor. Cell viability can be monitored using methods well known in the art.

Figure 1B:
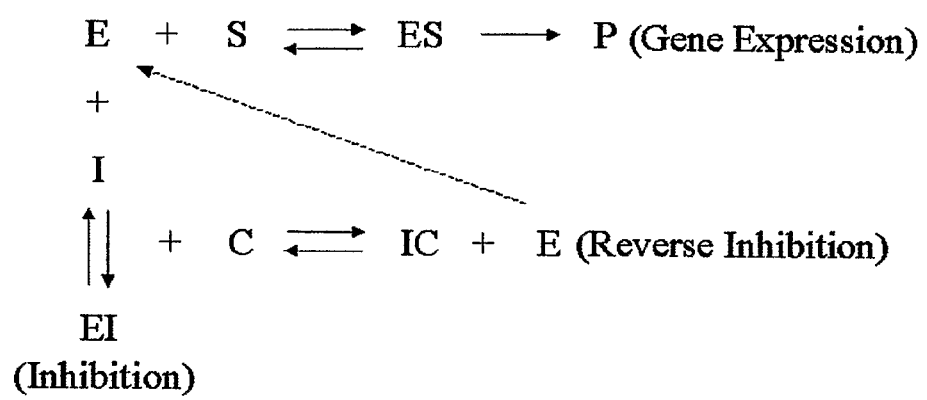

The increase in the level of gene expression upon addition of test compounds is referred to herein as "reverse inhibition", and forms a basis for the identification of molecules that modulate gene expression through direct interactions with the exogenously added RNA regulatory element. The proposed mechanism of reverse inhibition is shown in FIGS. 1A and 1B, descriptions for which are in the Brief Description of the Drawings.

Test compounds identified using the methods and systems of the present invention are useful as therapeutics for modulating the expression of genes that harbor the RNA elements(s) and whose expression is aberrant in the disease state (Mendell and Dietz, *Cell* 107: 411-414, 2001; Keene and Tenenbaum, Mol. Cell. 9:1161-1167, 2002), or whose expression causes the survival and/or progression of a pathogenic organism. Furthermore, said compounds are useful as molecular tools for regulating the expression of recombinant proteins expressed from constructs engineered to contain the RNA elements(s).

Description of Advantages to the Experimental Setup

In preferred embodiments of the invention, the RNA test sequence of interest, or a regulatory fragment thereof, is exogenously added to a cell-based translation system containing the reporter mRNA to assess inhibition of translation of the reporter. Once the RNA test sequence or fragment thereof is found to inhibit the translation of the reporter mRNA, the cell-based translation system including the inhibitory RNA test sequence and the reporter mRNA is contacted with a library of test compounds to assay for the reverse-inhibition of translation of the reporter mRNA.

The invention provides several significant advantages over previous approaches to identifying modulators of gene expression that target post-transcriptional regulation. One of the advantages over previous approaches is the present invention's ability to target both known and unknown RNA regulatory elements. Typical drug discovery systems (i.e., screens) for identifying modulators of gene expression that target post-transcriptional regulation require the identification and characterization of the RNA regulatory element and its interacting molecule(s). In all cases, the exact nature of the RNA regulatory element must first be known or determined before proceeding with the establishment of a screen to identify modulators.

The screening system for test compounds set forth herein requires only ability of the RNA test sequence or fragment thereof to inhibit translation when added exogenously to a cell-based translation system. Thus, the present invention is capable of combining a system of determining whether an RNA test sequence is involved in translational control with a rapid screening system for identifying compounds that interact with RNA regulatory elements and modulate gene expression. Because the two screening functions can be performed simultaneously with the systems and methods of the present invention, the speed and efficiency of therapeutic drug discovery are further increased.

Another advantage of the approach of the present invention is the specificity of its signal output. The present approach can detect specific interactions between the test compound and target RNA through an increase in signal from the reporter gene expression. Expression of the reporter mRNA increases when a compound interacts with the RNA test sequence so as to re-activate the components of the translational machinery and to allow translation of the reporter.

In contrast to many other approaches, the present invention detects neither reporter gene antagonists, nor reporter enzyme antagonists, both of which yield the typical false positive results in other assays that monitor a decrease in signal from the reporter gene expression (i.e., inhibition). For example, most assays feature a reporter enzyme coding sequence attached to a predetermined regulatory sequence of interest. The readout of such assays consists of a change in the expression of the reporter sequence upon addition of a test compound that interacts with the regulatory sequence of interest. However, a test compound that affects the enzymatic activity of the reporter instead of modulating the activity of the regulatory sequence generates a false positive or false negative signal in such assays. By contrast, in the systems and methods of the present invention, a test compound that inhibits the enzymatic activity of the reporter would correctly generate a negative result (decrease in signal or absence thereof) and be excluded from the target group of compounds that specifically interact with the regulatory RNA fragment.

In addition, most known assays detect cytotoxic agents and general inhibitors of translation as false positives in inhibition assays (including those not interacting with RNA), whereas in the present invention, such general inhibitors of translation are precluded from generating positive signals because they would also inhibit the translation of the reporter mRNA. Furthermore, in the present invention, interactions between the test compound and factors of the general translation machinery involved in inhibition would generate a negative result if they in turn have inhibitory effects on translation, leading to the appropriate exclusion of such nonspecific (and thereby toxic) agents from the target group of compounds.

Test compounds generate positive results in the systems and methods of the present invention if, and only if, they interfere with the interaction between the RNA regulatory sequence of interest and a component of the general translation machinery. Thus, test compounds identified by the present invention target specifically the RNA regulatory sequence of interest, leading to a dramatic reduction in the number of artificial results obtained in prior approaches. This advantageous feature of the present invention makes it particularly well suited to high-throughput screening for RNA-interacting molecules that modulate gene expression.

Finally, the systems and methods of the present invention can be performed under controlled and tunable conditions. Specifically, the reporter gene expression has a fixed window for reverse-inhibition, or reference range, that is determined through translation of reporter mRNA without the RNA regulatory element present. Having a fixed window for activation (i.e., 100% reverse-inhibition) allows one to rank-order active compounds based on their levels of reverse inhibition. Furthermore, by simply increasing or decreasing the amount of exogenously added inhibitory RNA, one is able to adjust the window of reverse-inhibition and, thereby, "tune" the stringency of the screen (i.e., the ability of the screen to observe positive signals). Thus, the specificity of the invention allows for the rapid generation of highly specific positive signals with rank-ordering ability, which is also highly desirable in high-throughput screening for RNA-interacting molecules that modulate gene expression.

Description of RNA Test Sequences and/or Candidate RNA Regulatory Elements

Examples of RNA regulatory elements from 5' UTRs, which are well known in the art include Iron response element (IRE), Internal ribosome entry site (IRES), upstream open reading frame (uORF), Male specific lethal element (MSL-2), G-quartet element, and 5'-terminal oligopyrimidine tract (TOP). See, for example, *Translational control of gene expression*, Sonenberg, Hershey, and Mathews, eds., CSHL Press, 2000. Examples of known 3' UTR regulatory elements include AU-rich elements (AREs), ARE enhancers, Selenocysteine insertion sequence (SEC'S), Histone stem loop, Cytoplasmic polyadenylation elements (CPEs), Nanos translational control element, Amyloid precursor protein element (APP), Translational regulation element (TGE)/direct repeat element (DRE), Bruno element (BRE), 15-lipoxygenase differentiation control element (15-LOX-DICE), and G-quartet element (Keene and Tenenbaum, Mol Cell 9:1161-1167, 2002).

In a preferred embodiment, known regulatory RNA sequences for use in the systems of the present invention include the internal ribosome entry sites (IRES), which are among the best characterized 5' UTR-based cis-elements of post-transcriptional gene expression control. IRES elements facilitate cap-independent translation initiation by recruiting ribosomes directly to the mRNA start codon, are commonly located in the 3' region of 5' UTR, and are frequently composed of several discrete sequences. IRESes do not share significant sequence homology, but do form distinct RNA tertiary structures. Some IRESes contain sequences complementary to 18S RNA and form stable complexes with the 40S ribosomal subunit and initiate assembly of a translationally competent complex. A classic example of an IRES is the internal ribosome entry site from Hepatitis C virus (HCV). Most known IRESes require protein co-factors for activity. More than 10 IRES trans-acting factors (ITAFs) have been identified so far. In addition, all canonical translation initiation factors, with the sole exception of 5' end cap-binding eIF4E, have been shown to participate in IRES-mediated translation initiation (reviewed in Vagner et al., EMBO reports 2:893-898, 2001; *Translational control of gene expression*, Sonenberg, Hershey, and Mathews, eds., CSHL Press, 2000).

In another preferred embodiment, known regulatory RNA sequences for use in the systems of the present invention are AU-rich elements (AREs). AU-rich elements are the most extensively studied 3' UTR-based regulatory signals. AREs are the primary determinant of mRNA stability and one of the key determinants of mRNA translation initiation efficiency. A typical ARE is 50 to 150 nucleotides long and contains 3 to 6 copies of an $AU_nA$ sequence (where n=3, 4, or 5) embedded in a generally A/U-enriched RNA region. The $AU_nA$ sequence be scattered within the region or can stagger or even overlap (Chen et al., TIBS 20:465-470, 1995; Wiklund et al., JBC 277:40462-40471, 2002; Tholanikunnel and Malborn, JBC 272:11471-11478, 1997; Worthington et al., JBC Sep. 24, 2002). The activity of certain AU-rich elements in promoting mRNA degradation is enhanced in the presence of distal uridine-rich sequences. These U-rich elements do not affect mRNA stability when present alone and thus that have been termed "ARE enhancers" (Chen et al., Mol. Cell. Biol. 14:416-426, 1994).

Most AREs function in mRNA decay regulation and/or translation initiation regulation by interacting with specific ARE-binding proteins (AUBPs). AUBP functional properties determine ARE involvement in one or both pathways. For example, ELAV/HuR binding to c-fos ARE inhibits c-fos mRNA decay (Brennan and Steitz, Cell Mol Life Sci. 58:266-277, 2001), association of tristetraprolin with TNFα ARE dramatically enhances TNFα mRNA hydrolysis (Carballo et al., Science 281:1001-1005, 1998), whereas interaction of TIA-1 with the TNFα ARE does not alter the TNFα mRNA stability but inhibits TNFα translation (Piecyk et al., EMBO J. 19:4154-4163, 2000). The competition of multiple AUBPs for the limited set of AUBP-binding sites in an ARE and the resulting "ARE proteome" determines the ARE regulatory output (Chen et al., Cell 107:451-464, 2001; Mukherjee et al., EMBO J. 21:165-174, 2002). Furthermore, the effects of AREs depends on ongoing translation (Curatola et al., Mol. Cell. Biol. 15:6331-6340, 1995; Chen et al., Mol. Cell. Biol. 15:5777-5788, 1995; Koeller et al., PNAS 88:7778-7782, 1991; Savant-Bhonsale et al., Genes Dev. 6:1927-1939, 1992; Aharon and Schneider, Mol. Cell. Biol. 13:1971-1980, 1993).

It is not clear how a 3' UTR-localized element can affect translation initiation—a process that takes place in the 5' UTR. One plausible explanation comes from recent work showing that most or all cytoplasmic mRNAs are circularized via eIF4F—poly(A)-binding protein (PABP) interaction; this interaction connects the two UTRs and can bring AREs in the 3' UTR into close proximity to the translation initiation site (Wells et al., Mol. Cell. 2:135-140, 1998). Thus, the translation machinery, in addition to its role in translating mRNA, can also serve as a destabilizing/ribonuclease-recruiting or a stabilizing/AUBPs-removing entity.

The methods and systems of the present invention can be applied to any target gene of interest. Specifically, the invention contemplates the identification of regulatory RNA sequences and the modulation by compounds identified by the instant methods of genes harboring these sequences that are involved in pathogenesis and pathophysiology.

Thus, for example, genes involved in carcinogenesis are suitable candidates for the methods and systems of the present invention. Such genes comprise oncogenes, i.e., genes associated with the stimulation of cell division, such as, but not limited to, genes coding for growth factors or receptors for growth factors, e.g., PDGF (brain and breast cancer), erb-B receptor for epidermal growth factor (brain and breast cancer), erb-B2 receptor for growth factor (breast, salivary, and ovarian cancers), RET growth factor receptor (thyroid cancer), Ki-ras activated by active growth factor receptor proteins (lung, ovarian, colon and pancreatic cancer), N-ras activated by active growth factor receptor proteins (leukemia's), c-src, a protein kinase that becomes overactive in phosphorylation of target proteins, transcription factors that activate growth promoting genes, such as c-myc which activates transcription of growth stimulation genes (leukemia, breast, stomach, and lung cancer), N-myc (nerve and brain cancer), L-myc (lung cancer), c-jun and c-fos, Bcl-2 which blocks cell suicide (lymphoma), Bcl-1 which codes for cyclin D1, a stimulatory protein of the cell cycle (breast, neck, head cancers), MDM2 which codes for antagonist of p53 (sarcomas).

Additionally, tumor suppressor genes, such as APC (colon and stomach cancers), DPC4 which is involved in cell division inhibitory pathway (pancreatic cancer), NF-1 which inhibits a stimulatory (Ras) protein (brain, nerve, and leukemia), NF-2 (brain and nerve cancers), MTS1 which codes for p16 which inhibits cyclin D-dependent kinase activity (many cancers), RB, a master brake on cell cycle (retinoblastoma, bone, bladder, lung, and breast cancer), p53 which halts cell cycle in G1 and induces cell suicide (many cancers), WT1 (Wilms tumor of the kidney), BRCA1 and 2 which function in repair of damage to DNA (breast and ovarian cancers), VHL (kidney cancer), telomerase which is involved in tumor cell immortality, thymidylate synthase and many more known to those of skill in the art.

In addition, genes coding for cytokines or virokines are also suitable targets for the methods and systems of the present invention. Both cytokines and virokines are well characterized in the art and available, for instance, from the Cytokines Online Pathfinder Encyclopaedia.

Genes involved in other pathophysiological processes, including viral genes (i.e. HIV, HCV and others) are either published in the literature and thus well known in the art and/or are easily identified by a person of skill. For example, if a gene involved in a particular disease process has not already been widely published, the National Cancer Institute's Cancer Genome Anatomy Project offers the Gene Ontology browser which classifies genes by molecular function, biological process, and cellular component, while the Human Gene Mutation database database can be searched either by disease, gene name or gene symbol. Due to the wealth of information about genes and their involvement in physiological processes as well as their dysregulation in disease that is available to a person skilled of art, it is evident that the systems and methods of the present invention can be practiced on any gene and its corresponding RNA sequence.

From the above, it is readily apparent that the instant invention is not limited to the use of UTRs, i.e. the untranslated sequences from the 5' cap to the start codon in case of a 5' UTR, or from the stop codon to the polyA tail in the case of a 3' UTR, but encompasses all mRNA fragments, even those potentially located within the coding sequence, that are capable of inhibiting translation when added exogenously. Thus, the invention allows not only the identification of novel RNA fragments able to inhibit the translation of the reporter mRNA, but also facilitates the characterization of the minimal regulatory elements contained within RNA sequences shown to be involved in translational control.

Accordingly, in another preferred embodiment of the present invention, synthetic RNA sequences are screened for the presence of regulatory elements. Chemical synthesis of oligonucleotides is a process well known in the art. The chemical synthesis can be that of DNA sequences which are subsequently transcribed into RNA by transcription described infra, or the synthesis can be of RNA directly. Synthetic RNA (or DNA) sequences can be produced by the random incorporation of all four natural nucleotides, as well as non-natural nucleotides known to those of skill in the art, at each coupling step of solid phase synthesis. In addition to the component bases, a number of reagents are used to assist in the formation of internucleotide bonds (e.g., oxidation, capping, detritylation, and deprotection). Automated synthesis is performed on a solid support matrix that serves as a scaffold for the sequential chemical reactions. (See also, *Oligonucleotide synthesis: A practical approach*, Atkinson T. and Smith M., IRL Press, Oxford, United Kingdom, 1984).

Synthetic RNA sequences that are identified by the methods and system of the present invention to include regulatory elements can be incorporated into expression vectors and used to increase the expression of recombinant proteins in both cell-based and in vitro translation systems. Thus, such RNA regulatory elements, although not necessarily occurring in nature, can be used to enhance the expression of recombinant protein products of interest in a variety of biotechnology applications.

Description of Isolation of Regulatory RNA Sequences

Identification and isolation of mRNA is well known to those of skill in the art. Thus, for example, the cDNAs obtained by reverse transcription of the mRNA obtained from any source, including viruses, pathogenic organisms, individual cells or whole tissue, can be generated by the use of primers that hybridize specifically to sequences in the polyA tail, thus resulting in a cDNA library. Moreover, cDNA libraries of many sources are also commercially available. The region of interest may then be amplified by PCR for use in the systems and methods of the present invention to obtain a DNA copy of the mRNA.

As discussed supra, many RNA regulatory elements are present in the untranslated regions of the mRNA. Thus, in a preferred embodiment of the present invention, a therapeutic gene of interest (or genome in the case of many viruses) is identified and its UTR sequences are located.

Identification of known UTRs can be conveniently performed by the use of bioinformatics, such as database mining from GENBANK, where sequences are annotated to delineate the coding portion from the non-coding portion of a gene. Alternatively, a known mRNA regulatory element may, for example, be selected from those made available by the European Bioinformatics Institute, the French Institute of Health and Medical Research, the UTR home page, a specialized sequence collection, deprived from redundancy, of 5' and 3' UTR sequences from eukaryotic mRNAs, a database that searches for similarity between a query sequence and 5' or 3' UTR sequences in UTRdb collections from Nucleic Acids Research, UTRSite (collection of functional sequence patterns located in 5' or 3' UTR sequences), UTRScan (looks for UTR functional elements by searching through user submitted query sequences for the patterns defined in the UTRsite collection), as well as UTRBlast, which searches for similarity between a query sequence and 5' or 3' UTR sequences in UTRdb collections, and other similar public databases and publications.

Alternatively, if the UTR sequences of the gene of interest are unknown, they can be identified experimentally by methods well known to those of skill in the art. For instance, the gene of interest can be cloned from a cDNA library and the ends of the cDNA can be amplified by RACE (rapid amplification of cDNA ends) and sequenced. Rapid Amplification of 5' cDNA Ends (5'-RACE) is used to extend partial cDNA clones by amplifying the 5' sequences of the corresponding mRNAs. The technique requires knowledge of a small region of sequence within the partial cDNA clone. During PCR, the thermostable DNA polymerase is directed to the appropriate target RNA by a single primer derived from the region of known sequence; the second primer required for PCR is complementary to a general feature of the target—in the case of 5'-RACE, to a homopolymeric tail added (via terminal transferase) to the 3' termini of cDNAs transcribed from a preparation of mRNA. This synthetic tail provides a primer-binding site upstream of the unknown 5' sequence of the target mRNA. Rapid Amplification of 3' cDNA Ends (3'-RACE) reactions are used to isolate unknown 3' sequences or to map the 3' termini of mRNAs onto a gene sequence. A population of mRNAs is transcribed into cDNA with an adaptor-primer consisting at its 3' end of a poly(T) tract and at its 5' end of an arbitrary sequence of 30-40 nucleotides. Reverse transcription is usually followed by two successive PCRs. The first PCR reaction is primed by a gene-specific sense oligonucleotide and an antisense primer complementary to the arbitrary sequence in the (dT) adaptor-primer. If necessary, the products of the first PCR can be used as templates for a second "nested" PCR, which is primed by a gene-specific sense oligonucleotide internal to the first, and a second antisense oligonucleotide complementary to the central region of the (dT) adaptor-primer. The products of the amplification reaction are cloned into a plasmid vector for sequencing and subsequent manipulation.

Furthermore, the present invention allows the identification of RNA regulatory elements present within the coding, or translated, sequence of mRNAs of genes of interest. Because the coding sequence of a gene of interest is easily obtained, as it is typically the primary subject of publication in journals and public databases, the foregoing description of the isolation of an RNA sequence or region of interest applies, in simplified form, to RNA coding sequences as well.

Once the RNA sequence or region of interest has been isolated, it can then be analyzed for the presence of known regulatory sequences that can be synthesized for use in the systems and methods of the present invention. Search algorithms such as BLAST allow one skilled in the art to identify sequences with homology to the regulatory sequences of interest. If no known regulatory sequences are present in the RNA regions, the entire RNA sequence, UTR element and/or fragments thereof can be synthesized for use in the present invention. The secondary structure of single-stranded RNA can be analyzed in silico to identify regions of the RNA that are likely to fold into higher order structures and, thereby, perform a regulatory function using algorithms provided by, for example, M-FOLD, RNA structure (Zuker algorithm), Vienna RNA Package, RNA Secondary Structure Prediction (Belozersky Institute, Moscow, Russia) and ESSA, among many known algorithms. These higher order structures include harpins, stem-loops, bulges, pseudoknots, guanosine quartets, and turns (for reviews see Moore, Ann. Rev. Biochem. 68: 287-300, 1999; Gallego and Varani, Acc. Chem.

Res. 34, 836-843, 2001). An analysis of the higher order structures revealed by in silico predictions allows a person skilled in the art to design primers that are complementary to inter-domain regions of the sequence for use in PCR amplification and subsequent cloning for fragment generation.

RNA fragments can be prepared by a variety of techniques known to those of skill in the art. Run-off transcription from a cloned DNA template can be performed by the use of in vitro transcription methods known to those of skill in the art (Srivastava et al., Methods Mol. Biol. 86:201-207, 1998); commercially available in vitro transcription kits, such as Megascript™ from Ambion (Austin, Tex.) which uses T7 RNA polymerase to transcribe RNA from DNA templates harboring a T7 promoter in high yields can also be used. Transcription from a cloned DNA template can also be performed by the use of cell-based transcription methods known to those skilled in the art. To generate a cloned DNA template, one skilled in the art can readily design primers that hybridize to the 5' and 3' end portions of the specific region(s) of interest from a full-length cDNA clone. Use of these primers for PCR amplification, and subsequent cloning into a vector downstream of a suitable promoter sequence, is readily performed by a person skilled in the art. Alternatively, solid-phase oligonucleotide synthesis can be performed using phosphoramidite chemistry, and custom synthesis of RNA oligos is commercially available (Dharmacon Research, Inc., Lafayette, Colo.).

In another preferred embodiment, the invention provides an RNA regulatory sequence in combination with its specific regulatory protein co-factor(s) for use in the screen. If the regulatory co-factor is known, those of skill in the art, using recombinant techniques, can readily prepare it. Alternatively, the RNA regulatory sequence of interest may be isolated as described supra and immobilized to a solid-phase support by methods known to those of skill in the art (e.g., affinity-tag). Upon addition of cellular extract, the RNA regulatory sequence will retain the factor(s) specifically able to bind the immobilized RNA sequence, whether known or unknown, and all other factors will be removed. The combination of RNA regulatory sequence with its specific regulatory co-factor can then be eluted from the solid-phase support for use in the system of the present invention. Use of the regulatory RNA sequence in conjunction with its regulatory co-factor will allow for the identification of test compounds that interfere with the interaction between the RNA regulatory element (in combination with its specific regulatory co-factor) and components of the general translation machinery.

Description of Reporter mRNAs

In one embodiment of the systems and methods of the present invention, the cells employed constitutively express reporter mRNA.

In another embodiment of the present invention, a reporter mRNA construct is exogenously added to the cells (e.g., via transfection of the reporter mRNA or a DNA copy of the reporter mRNA). Synthesis of reporter constructs is well known in the art and can be performed as described above for the synthesis of the regulatory RNA sequences, e.g., in vitro T7 promoter-driven run-off transcription from linear DNA templates using T7 RNA polymerase, or cell-based promoter-driven transcription from transfected DNA templates. In one embodiment of the present invention, the DNA templates contain a promoter sequence and a protein coding sequence to express the reporter protein. The reporter is preferably constructed to contain no translational regulatory elements and, thereby, monitors general translation efficiency.

The reporter mRNA can be selected from known reporters in the art, including but not limited to, firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, secreted alkaline phosphatase, or horseradish peroxidase.

In the methods of the present invention, a measurable signal can be detected, which results from gene expression of the reporter mRNA. For example, the signal can be selected from, but is not limited to: enzymatic activity, fluorescence, bioluminescence and combinations thereof.

In one embodiment of the method to screen for RNA regulatory elements, enzymatic activity resulting from gene expression of the reporter mRNA in the presence of an RNA test sequence is measured and compared to the enzymatic activity which results from gene expression of the reporter mRNA in the absence of the RNA test sequence. In one embodiment of the methods to screen for test compounds that influence/modulate the regulatory activity of an RNA regulatory sequence, enzymatic activity resulting from gene expression of the reporter mRNA in the presence of the test compound(s) is measured and compared to the enzymatic activity in the absence of the test compound(s).

Translation of reporter mRNA and subsequent incubation with the enzyme substrate allows for the quantitative analysis of gene expression through the detection of reaction products. In preferred embodiments, the protein coding sequence of firefly luciferase is used in the reporter construct, an example of a substrate for which is luciferin, a pigment which turns over to make visible light known as bioluminescence.

Description of the Cells and Cell-Based Translation System

The systems and methods of the present invention feature a cell-based translation system. Useful cells for purposes of the present invention include, but are not limited to, the following: human, yeast, amphibian, bacterial, plant and animal cells, such as cells from mammals including mouse, hamster or rabbit.

In preferred embodiments of the invention, the cells are mammalian cells. Mammalian cell lines available as hosts for expression are known in the art and include many immortalized cell lines available from the cell depository AMERICAN TYPE CULTURE COLLECTION (ATCC™, Manassas, Va.), such as HeLa cells, Chinese hamster ovary (CHO) cells, baby hamster kidney (BHK) cells and a number of other cell lines. Non-limiting examples of suitable mammalian host cell lines include those shown below in Table 1.

TABLE 1

Mammalian Host Cell Lines

| Host Cell | Origin | Source |
|---|---|---|
| HepG-2 | Human Liver Hepatoblastoma | ATCC ™ (cell depository) HB 8065 |
| CV-1 | African Green Monkey Kidney | ATCC ™ (cell depository) CCL 70 |
| LLC-MK$_2$ | Rhesus Monkey Kidney | ATCC ™ (cell depository) CCL 7 |

TABLE 1-continued

Mammalian Host Cell Lines

| Host Cell | Origin | Source |
|---|---|---|
| 3T3 | Mouse Embryo Fibroblasts | ATCC ™ (cell depository) CCL 92 |
| AV12-664 | Syrian Hamster | ATCC ™ (cell depository) CRL 9595 |
| HeLa | Human Cervix Epitheloid | ATCC ™ (cell depository) CCL 2 |
| RPMI8226 | Human Myeloma | ATCC ™ (cell depository) CCL 155 |
| H4IIEC3 | Rat Hepatoma | ATCC ™ (cell depository) CCL 1600 |
| C127I | Mouse Fibroblast | ATCC ™ (cell depository) CCL 1616 |
| 293 | Human Embryonal Kidney | ATCC ™ (cell depository) CRL 1573 |
| HS-Sultan | Human Plasma Cell Plasmocytoma | ATCC ™ (cell depository) CCL 1484 |
| BHK-21 | Baby Hamster Kidney | ATCC ™ (cell depository) CCL 10 |
| CHO-K1 | Chinese Hamster Ovary | ATCC ™ (cell depository) CCL 61 |

In some embodiments, human cells are preferred (for example, HeLa, HEL, MRC-5, NHFL, HCT 116, HEK 293, HEK 293T, Jurkat, human foreskin fibroblasts (HFF), A 549, Caco-2). In some other embodiments, the cells are monkey cells (for example, COS-1, COS-7, CV-1), yeast cells, mouse cells (for example, F9, L929, McCoy, MNA, NIH 373), rat cells (for example, PC-12), Chinese hamster ovary cells, Xenopus oocytes, reticulocytes, or bacterial cells. For example, rabbit reticulocytes (RRL) are well known in the art and are commercially available. Rabbit reticulocytes are highly efficient eukaryotic protein synthesis systems used for the translation of exogenous RNAs (either natural or generated in vitro). Because reticulocytes are highly specialized cells that manufacture large amounts of hemoglobin, a reticulocyte-based translation system is highly enriched for specific components of the general translation machinery.

A cell-line/strain for use in the methods and systems of the present invention can contain a genomic copy(s) of the reporter mRNA under the control of a constitutively active promoter sequence for expression of the reporter mRNA. For example, a DNA copy of the reporter mRNA under the control of a constitutively active promoter (e.g., SV40, CMV, RSV) can be exogenously added (e.g., via transfection) to the cells. The cell lines described above, including those listed in Table 1 may be used. The promoter sequence will attract RNA polymerase and lead to the production of the reporter mRNA. The cell's ribosomes will translate the mRNA into the reporter protein.

Cells for use in the methods and systems of this invention can contain a stably integrated genomic copy(s) of an RNA regulatory sequence, under the control of an inducibly active promoter sequence (e.g., Clontech Tet-On™ or Tet-Off™ vectors allow for inducible expression). Addition of the appropriate chemical inducer facilitates temporal transcription of the RNA regulatory sequence.

Alternatively, the regulatory RNA fragment can be added to the cell-based translation system exogenously using transfection techniques. Moreover, a DNA copy of the regulatory RNA sequence under the control of a constitutively active promoter sequence can be added to the cell-based translation system exogenously using transfection techniques to facilitate transient expression. Techniques used to introduce nucleic acids into cell-based systems are well known to those skilled in the art (e.g., liposome-mediated transfection or calcium phosphate-mediated transfection).

Description of the Experimental Setup

In one embodiment of the method for screening for and/or identifying an RNA regulatory sequence, the experimental setup first entails the selection of an RNA test sequence. Such a test sequence may be a synthetic sequence or a naturally occurring sequence present in a therapeutic gene of interest (or genome in the case of some pathogenic organisms), the expression of which would advantageously be modulated by small-molecule intervention at the post-transcriptional level.

A DNA copy of the RNA test sequence can be transfected into the cells for expression of the RNA test sequence, wherein the test sequence DNA is under the control of a constitutively active promoter. Transfected DNA can either be transiently expressed or permanently expressed. DNA that has crossed the membrane barrier will be transported into the nucleus where it will be transcribed if it contains a suitable promoter.

Alternatively, the RNA test sequence can be synthesized and then transfected into the cells. By its very nature, RNA transfection is typically used for transient expression.

In the case of a sequence of a gene of interest, the RNA regulatory elements can be identified and the target RNA sequence can be synthesized in sufficient quantities for use in the systems/methods of the present invention by run-off transcription (Megascript™, Ambion Inc., Austin, Tex.). Full-length RNA sequences of interest, as well as fragments thereof, can be prepared to identify the minimal construct required for translation regulation. Subsequently, the target RNA can be heat denatured and cooled to form stable secondary structure, after which time it can be transfected into the cells.

Similarly, the synthesis of the reporter mRNA can be performed by run-off transcription. The mRNA reporter construct can then be expressed in a cell-based translation system. Appropriate DNA copies of the reporter RNA can be prepared for use in cell-based translation systems. Alternatively, the cells employed in the methods and systems of the present invention can contain a genomic copy of the reporter mRNA under the control of a constitutively active promoter sequence for expression of the reporter mRNA.

In one embodiment of the present invention, the inhibitory activity of the RNA test sequence or fragments thereof is first evaluated in cells. In one example, this entails contacting the cell-based translation system with each of the RNA test sequences and/or fragments to be tested, contacting the reporter with the translation system (pre-treated with each of the RNA test sequences and/or fragments thereof) and selecting the minimal fragment required for efficient inhibition. Inhibition of general translation due to the RNA test sequence can be monitored through either reporter gene expression measurements or cell viability measurements. The cells employed can contain a genomic copy of the reporter mRNA. Alternatively, the reporter mRNA or a DNA copy thereof can be exogenously added to the cells.

RNA sequences which were identified by the present in vivo methods to include regulatory elements, or known RNA regulatory sequences can be used in methods of the present invention to screen test compounds for their ability to modulate post-transcriptional gene expression. In addition to the present in vivo methods, it is noted that it is also within the contemplation of the present invention that the inhibitory activity of the RNA test sequence can first be evaluated in vitro using, for example, the methods described in PCT/US2004/00023, filed Jan. 9, 2004.

RNA regulatory sequences can be incorporated into the genome of cells, the genomic copy being under the control of an inducibly active promoter sequence. Such cells can be employed in the methods and systems of the present invention to identify test compounds for modulating the expression of genes that harbor the RNA regulatory element(s), wherein the RNA regulatory sequence is introduced via inducible transcription. Alternatively, constructs can be engineered to contain the RNA element(s) and the RNA regulatory sequence can be introduced into the cells via exogenous addition (e.g., via transfection) of the RNA regulatory sequence or a DNA copy thereof.

As described above, the cell-based translation system, minimal inhibitory RNA fragment, and reporter can be contacted with a library of test compounds. Specifically, in one embodiment, the test compound is added to the cells including the cell-based translation system and the genomic copy of the reporter mRNA; and the RNA fragment is introduced to the system (either through exogenous addition of the RNA fragment, through exogenous addition of a DNA copy of the RNA fragment, or through inducible transcription). The cells are incubated for a set period of time, and the reverse inhibitors are identified by the presence of the signal produced by the translation of the reporter RNA that was previously suppressed, in the absence of the test compound, by the presence of the minimal inhibitory RNA fragments. Alternatively, the reverse inhibitors can be identified by cell viability measurements.

Finally, the structure of the test compound that resulted in altered expression can be determined, leading to secondary screens with mRNA constructs that harbor the regulatory RNA sequence and, ultimately, to the development of important new compounds for molecular medicine and biotechnology.

Description of Compound Libraries

Libraries screened using the methods of the present invention can comprise a variety of types of test compounds. In some embodiments, the test compounds are nucleic acid or peptide molecules. In a non-limiting example, peptide molecules can exist in a phage display library. In other embodiments, types of test compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used.

In a preferred embodiment, the combinatorial libraries are small organic molecule libraries, such as, but not limited to, benzodiazepines, isoprenoids, thiazolidinones, metathiazanones, pyrrolidines, morpholino compounds, and diazepindiones. In another embodiment, the combinatorial libraries comprise peptoids; random bio-oligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, for e.g., Advanced ChemTech Europe Ltd., Cambridgeshire, UK; ASINEX, Moscow, Russia; BioFocus plc, Sittingbourne, UK; Bionet Research (A division of Key Organics Limited), Camelford, UK; ChemBridge Corporation, San Diego, Calif.; ChemDiv Inc, San Diego, Calif.; ChemRx Advanced Technologies, South San Francisco, Calif.; ComGenex Inc., Budapest, Hungary; Evotec OAI Ltd, Abingdon, UK; IF LAB Ltd., Kiev, Ukraine; Maybridge plc, Cornwall, UK; PharmaCore, Inc., North Carolina; SIDDCO Inc, Tucson, Ariz.; TimTec Inc, Newark, Del.; Tripos Receptor Research Ltd, Bude, UK; Toslab, Ekaterinburg, Russia).

In one embodiment, the combinatorial compound library for the methods of the present invention may be synthesized. There is a great interest in synthetic methods directed toward the creation of large collections of small organic compounds, or libraries, which could be screened for pharmacological, biological or other activity (Dolle J., Comb. Chem. 3:477-517, 2001; Hall et al., J. Comb. Chem. 3:125-150, 2001; Dolle J., Comb. Chem. 2:383-433, 2000; Dolle J., Comb. Chem. 1:235-282, 1999). The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry. Methods and strategies for the synthesis of combinatorial libraries can be found in *A Practical Guide to Combinatorial Chemistry*, A. W. Czarnik and S. H. Dewitt, eds., American Chemical Society, 1997; *The Combinatorial Index*, B. A. Bunin, Academic Press, 1998; *Organic Synthesis on Solid Phase*, F. Z. Dörwald, Wiley-VCH, 2000; and *Solid-Phase Organic Syntheses, Vol. I*, A. W. Czarnik, ed., Wiley Interscience, 2001.

Combinatorial compound libraries of the present invention may be synthesized using apparatuses described in U.S. Pat. No. 6,358,479 to Frisina et al., U.S. Pat. No. 6,190,619 to Kilcoin et al., U.S. Pat. No. 6,132,686 to Gallup et al., U.S. Pat. No. 6,126,904 to Zuellig et al., U.S. Pat. No. 6,074,613 to Harness et al., U.S. Pat. No. 6,054,100 to Stanchfield et al., and U.S. Pat. No. 5,746,982 to Saneii et al. which are hereby incorporated by reference in their entirety. These patents describe synthesis apparatuses capable of holding a plurality of reaction vessels for parallel synthesis of multiple discrete compounds or for combinatorial libraries of compounds. In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid-phase synthesis of combinatorial compound libraries, liquid phase synthesis does not require the use of specialized protocols for monitoring the individual steps of a multi-step solid-phase synthesis (Egner et al., J. Org. Chem. 60:2652, 1995; Anderson et. al., J. Org. Chem. 60:2650, 1995; Fitch et al., J. Org. Chem. 59:7955, 1994; Look et al., J. Org. Chem. 49:7588, 1994; Metzger et al., Angew. Chem., Int. Ed. Engl. 32:894, 1993; Youngquist et. al., Rapid Commun. Mass Spect. 8:77-81, 1994; Chu et al., J. Am. Chem. Soc. 117:5419, 1995; Brummel et al., Science 264:399-402, 1994; Stevanovic et al., Bioorg. Med. Chem. Lett. 3:431, 1993).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see Lam et al., Chem. Rev. 97:411-448, 1997; Ohlmeyer et al., Proc. Natl. Acad. Sci. USA 90:10922-10926, 1993 and references cited therein). Each solid support in the final library has substantially one type of test compound attached to its surface. Other methods for synthesizing combinatorial libraries on solid supports, wherein one product is attached to each support, will be known to those of skill in the art (see, e.g., Nefzi et al., Chem. Rev. 97:449-472, 1997 and U.S. Pat. No. 6,087,186 to Cargill et al. which are hereby incorporated by reference in their entirety). As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p methylbenzhydrylamine (pMBHA) resin (Peptides International, Louisville, Ky.), polystyrenes (e.g., PAM-resin obtained from Bachem Inc., Torrance, Calif., Peninsula Laboratories, San Carlos, Calif., etc.), including chloromethylpolystyrene, hydroxymethylpolystyrene and aminomethylpolystyrene, poly (dimethylacrylamide) grafted styrene co-divinyl-benzene (e.g., POLYHIPE resin, obtained from Aminotech, Ontario, Canada) polyamide resin (obtained from Peninsula Laboratories, San Carlos, Calif.), polystyrene resin grafted with polyethylene glycol (e.g., TENTA-GEL or ARGOGEL, Bayer, Tubingen, Germany) polydimethylacrylamide resin (obtained from Milligen/Biosearch, California), or Sepharose (Pharmacia, Sweden).

In one embodiment, the solid phase support is suitable for in vivo use, i.e. it can serve as a carrier or support for administration of the test compound to a patient (e.g., TENTAGEL, Bayer, Tubingen, Germany). In a particular embodiment, the solid support is palatable and/or orally ingestable. In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of test compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions.

In another embodiment, the combinatorial compound libraries can be assembled in situ using dynamic combinatorial chemistry as described in European Patent Application 1,118,359 A1 to Lehn; Huc & Nguyen Comb. Chem. High Throughput. Screen. 4:53-74, 2001; Lehn and Eliseev, Science 291:2331-2332, 2001; Cousins et al., Curr. Opin. Chem. Biol. 4: 270-279, 2000; and Karan & Miller, Drug. Disc. Today 5:67-75, 2000 which are incorporated by reference in their entirety. Dynamic combinatorial chemistry uses non-covalent interaction with a target biomolecule, including but not limited to a protein, RNA, or DNA, to favor assembly of the most tightly binding molecule that is a combination of constituent subunits present as a mixture in the presence of the biomolecule. According to the laws of thermodynamics, when a collection of molecules is able to combine and recombine at equilibrium through reversible chemical reactions in solution, molecules, preferably one molecule, that bind most tightly to a templating biomolecule will be present in greater amount than all other possible combinations. The reversible chemical reactions include, but are not limited to, imine, acyl-hydrazone, amide, acetal, or ester formation between carbonyl-containing compounds and amines, hydrazines, or alcohols; thiol exchange between disulfides; alcohol exchange in borate esters; Diels-Alder reactions; thermal- or photoinduced sigmatropic or electrocyclic rearrangements; or Michael reactions.

In the preferred embodiment of this technique, the constituent components of the dynamic combinatorial compound library are allowed to combine and reach equilibrium in the absence of the target RNA and then incubated in the presence of the target RNA, preferably at physiological conditions, until a second equilibrium is reached. The second, perturbed, equilibrium (the so-called "templated mixture") can, but need not necessarily, be fixed by a further chemical transformation, including but not limited to reduction, oxidation, hydrolysis, acidification, or basification, to prevent restoration of the original equilibrium when the dynamical combinatorial compound library is separated from the target RNA. In the preferred embodiment of this technique, the predominant product or products of the templated dynamic combinatorial library can separated from the minor products and directly identified.

In another embodiment, the identity of the predominant product or products can be identified by a deconvolution strategy involving preparation of derivative dynamic combinatorial libraries, as described in European Patent Application 1,118,359 A1, which is incorporated by reference in its entirety, whereby each component of the mixture is, preferably one-by-one but possibly group-wise, left out of the mixture and the ability of the derivative library mixture at chemical equilibrium to bind the target RNA is measured. The components whose removal most greatly reduces the ability of the derivative dynamic combinatorial library to bind the target RNA are likely the components of the predominant product or products in the original dynamic combinatorial library.

Description of Methods for Determining the Structure of the Test Compound

If the library comprises arrays or microarrays of compounds, wherein each compound has an address or identifier, the compound can be deconvoluted, e.g., by cross-referencing the positive sample to original compound list that was applied to the individual test assays. If the library is a peptide or nucleic acid library, the sequence of the compound can be determined by direct sequencing of the peptide or nucleic acid. Such methods are well known to one of skill in the art. A number of physico-chemical techniques can be used for the de novo characterization of compounds bound to the target RNA. Examples of such techniques include, but are not limited to, mass spectrometry, NMR spectroscopy, X-ray crystallography and vibrational spectroscopy. The characterization of compounds bound to the target RNA allows for the identification of active molecules from mixtures obtained from combinatorial chemistry libraries.

Mass Spectrometry

Mass spectrometry (e.g., electrospray ionization ("ESI"), matrix-assisted laser desorption-ionization ("MALDI"), and Fourier-transform ion cyclotron resonance ("FT-ICR") can be used for elucidating the structure of a compound. MALDI uses a pulsed laser for desorption of the ions and a time-of-flight analyzer, and has been used for the detection of noncovalent tRNA:amino-acyl-tRNA synthetase complexes (Gruic-Sovulj et al., J. Biol. Chem. 272:32084-32091, 1997). However, covalent cross linking between the target nucleic acid and the compound is required for detection, since a non-covalently bound complex may dissociate during the MALDI process. ESI mass spectrometry ("ESI-MS") has been of greater utility for studying non-covalent molecular interactions because, unlike the MALDI process, ESI-MS generates molecular ions with little to no fragmentation (Xavier et al., Trends Biotechnol. 18(8):349-356, 2000). ESI MS has been used to study the complexes formed by HIV Tat peptide and protein with the TAR RNA (Sannes-Lowery et al., Anal. Chem. 69:5130-5135, 1997). Fourier-transform ion cyclotron resonance ("FT-ICR") mass spectrometry provides high-resolution spectra, isotope-resolved precursor ion selection, and accurate mass assignments (Xavier et al., Trends Biotechnol. 18(8):349-356, 2000). FT-ICR has been used to study the interaction of aminoglycoside antibiotics with cognate and non-cognate RNAs (Hofstadler et al., Anal. Chem. 71:3436-3440, 1999; and Griffey et al., Proc. Natl. Acad. Sci. USA 96:10129-10133, 1999). As true for all of the mass spectrometry methods discussed herein, FT-ICR does not require labeling of the target RNA or a compound. An advantage of mass spectroscopy is not only the elucidation of the structure of the compound, but also the determination of the structure of the compound bound to a target RNA. Such information can enable the discovery of a consensus structure of a compound that specifically binds to a target RNA.

NMR Spectroscopy

NMR spectroscopy is a valuable technique for identifying complexed target nucleic acids by qualitatively determining changes in chemical shift, specifically from distances measured using relaxation effects, and NMR-based approaches have been used in the identification of small molecule binders of protein drug targets (Xavier et al., Trends Biotechnol. 18(8):349-356, 2000). The determination of structure-activity relationships ("SAR") by NMR is the first method for NMR described in which small molecules that bind adjacent subsites are identified by two-dimensional 1H-15N spectra of the target protein (Shuker et al., Science 274:1531-1534, 1996). The signal from the bound molecule is monitored by employing line broadening, transferred NOEs and pulsed field gradient diffusion measurements (Moore, Curr. Opin. Biotechnol. 10:54-58, 1999).

A strategy for lead generation by NMR using a library of small molecules has been recently described (Fejzo et al., Chem. Biol. 6:755-769, 1999). In one embodiment of the present invention, the target nucleic acid complexed to a compound can be determined by SAR by NMR. Furthermore, SAR by NMR can also be used to elucidate the structure of a compound. As described above, NMR spectroscopy is a technique for identifying binding sites in target nucleic acids by qualitatively determining changes in chemical shift, specifically from distances measured using relaxation effects.

Examples of NMR that can be used for the invention include, but are not limited to, one-dimensional NMR, two-dimensional NMR, correlation spectroscopy ("COSY"), and nuclear Overhauser effect ("NOE") spectroscopy. Such methods of structure determination of compounds are well-known to one of skill in the art. Similar to mass spectroscopy, an advantage of NMR is the not only the elucidation of the structure of the compound, but also the determination of the structure of the compound bound to the target RNA. Such information can enable the discovery of a consensus structure of a compound that specifically binds to a target RNA.

X-Ray Crystallography

X-ray crystallography can be used to elucidate the structure of a compound. For a review of x-ray crystallography see, e.g., Blundell et al., Nat Rev Drug Discov 1(1):45-54, 2002. The first step in x-ray crystallography is the formation of crystals. The formation of crystals begins with the preparation of highly purified and soluble samples. The conditions for crystallization are then determined by optimizing several solution variables known to induce nucleation, such as pH, ionic strength, temperature, and specific concentrations of organic additives, salts and detergent. Techniques for automating the crystallization process have been developed for the production of high-quality protein crystals. Once crystals have been formed, the crystals are harvested and prepared for data collection. The crystals are then analyzed by diffraction (such as multi-circle diffractometers, high-speed CCD detectors, and detector off-set). Generally, multiple crystals must be screened for structure determinations.

Vibrational Spectroscopy

Vibrational spectroscopy (e.g. infrared (IR) spectroscopy or Raman spectroscopy) can be used for elucidating the structure of a compound. Infrared spectroscopy measures the frequencies of infrared light (wavelengths from 100 to 10,000 nm) absorbed by the compound as a result of excitation of vibrational modes according to quantum mechanical selection rules which require that absorption of light cause a change in the electric dipole moment of the molecule. The infrared spectrum of any molecule is a unique pattern of absorption wavelengths of varying intensity that can be considered as a molecular fingerprint to identify any compound. Infrared spectra can be measured in a scanning mode by measuring the absorption of individual frequencies of light, produced by a grating which separates frequencies from a mixed frequency infrared light source, by the compound relative to a standard intensity (double-beam instrument) or pre-measured ('blank') intensity (single-beam instrument).

In a preferred embodiment, infrared spectra are measured in a pulsed mode ("FT-IR") where a mixed beam, produced by an interferometer, of all infrared light frequencies is passed through or reflected off the compound. The resulting interferogram, which may or may not be added with the resulting interferograms from subsequent pulses to increase the signal strength while averaging random noise in the electronic signal, is mathematically transformed into a spectrum using Fourier Transform or Fast Fourier Transform algorithms.

Raman spectroscopy measures the difference in frequency due to absorption of infrared frequencies of scattered visible or ultraviolet light relative to the incident beam. The incident monochromatic light beam, usually a single laser frequency, is not truly absorbed by the compound but interacts with the electric field transiently. Most of the light scattered off the sample will be unchanged (Rayleigh scattering) but a portion of the scatter light will have frequencies that are the sum or difference of the incident and molecular vibrational frequencies. The selection rules for Raman (inelastic) scattering require a change in polarizability of the molecule.

While some vibrational transitions are observable in both infrared and Raman spectrometry, most are observable only with one or the other technique. The Raman spectrum of any molecule is a unique pattern of absorption wavelengths of varying intensity that can be considered as a molecular fingerprint to identify any compound. Raman spectra are measured by submitting monochromatic light to the sample, either passed through or preferably reflected off, filtering the Rayleigh scattered light, and detecting the frequency of the Raman scattered light. An improved Raman spectrometer is described in U.S. Pat. No. 5,786,893 to Fink et al., which is hereby incorporated by reference. Vibrational microscopy can be measured in a spatially resolved fashion to address single beads by integration of a visible microscope and spectrometer. A microscopic infrared spectrometer is described in U.S. Pat. No. 5,581,085 to Reffner et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety.

In one embodiment of the method, compounds are synthesized on polystyrene beads doped with chemically modified styrene monomers such that each resulting bead has a characteristic pattern of absorption lines in the vibrational (IR or Raman) spectrum, by methods including but not limited to those described by Fenniri et al., J. Am. Chem. Soc. 123: 8151-8152, 2000. Using methods of split-pool synthesis familiar to one of skill in the art, the library of compounds is prepared so that the spectroscopic pattern of the bead identifies one of the components of the compound on the bead. Beads that have been separated according to their ability to bind target RNA can be identified by their vibrational spectrum. In one embodiment of the method, appropriate sorting and binning of the beads during synthesis then allows identification of one or more further components of the compound on any one bead. In another embodiment of the method, partial identification of the compound on a bead is possible through use of the spectroscopic pattern of the bead with or without the aid of further sorting during synthesis, followed by partial resynthesis of the possible compounds aided by doped beads and appropriate sorting during synthesis. In another embodiment, the IR or Raman spectra of compounds are examined while the compound is still on a bead, preferably, or after cleavage from bead, using methods including but not limited to photochemical, acid, or heat treatment. The compound can be identified by comparison of the IR or Raman spectral pattern to spectra previously acquired for each compound in the combinatorial library.

EXAMPLES

The following examples are provided to better illustrate the claimed invention and are not to be interpreted as limiting the scope of the invention. To the extent that specific materials are mentioned, it is merely for purposes of illustration and is not intended to limit the invention. Unless otherwise specified, general cloning procedures are used, such as those set forth in the following: Sambrook et al., Molecular Cloning, Cold Spring Harbor Laboratory, 2001, Ausubel et al. (eds.); and Current Protocols in Molecular Biology, John Wiley & Sons, 2000. One skilled in the art may develop equivalent means or reactants without departing from the scope of the invention.

It is noted that the examples below provide systems and assays for use in 6-well, 96-well or 60 mm culture dishes. However, the present systems and methods can be scaled-up and adapted for use in high-throughput screenings, such as those conducted in a 384-well format.

Example 1

Construction of the Reporter mRNA

This example illustrates the construction of the reporter mRNA to determine the level of reverse inhibition of translation. The reporter plasmid pT7 is constructed to contain the following elements: T7 promoter sequence and multiple cloning site (MCS). The non-natural MCS sequences used for the initial insertion of the Luciferase open reading frame (ORF) can also be used for generating fusion proteins. The plasmid pT7-luc contains the protein coding sequence of firefly luciferase cloned downstream of the T7 promoter sequence at the NcoI and BglII restriction endonuclease sites.

Figure 3:
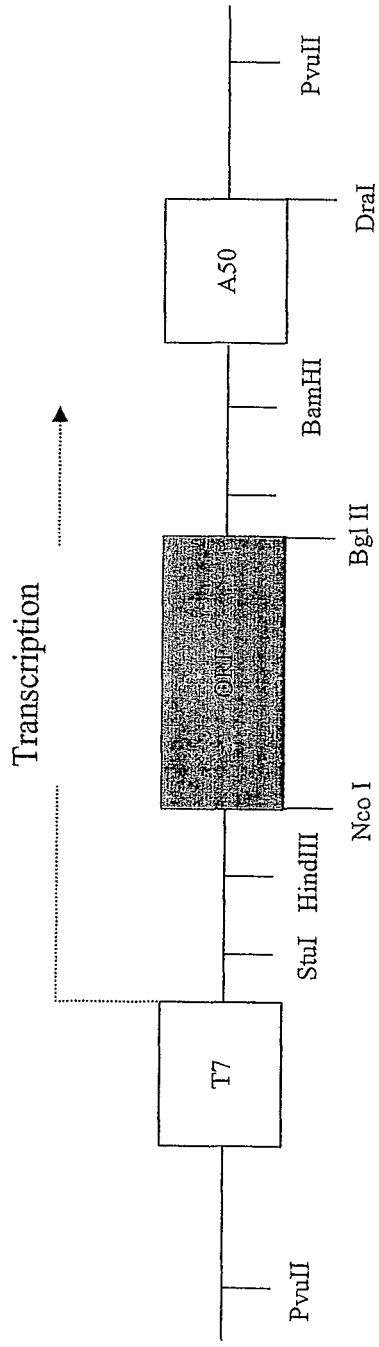
FIG. 3. This figure shows the components of an exemplary reporter DNA construct used to produce reporter mRNA for use in the identification of compounds with the ability to reverse inhibition of translation. This reporter uses the open reading frame (ORF) of firefly luciferase fused to a consensus T7 promoter sequence at the NcoI and BglII restriction endonuclease cleavage sites and is devoid of any predicted RNA regulatory elements. The linearized template used for run-off transcription of mRNA is generated by restriction endonuclease digestion at the BamH1 site. The resulting transcription product is purified by precipitation with LiCl and is used without further modification.

FIG. 3 shows the components of an exemplary reporter DNA construct used to produce reporter mRNA for use in the methods of the present invention, a description for which is in the Brief Description of the Drawings. The plasmid pT7-luc was digested with BamH1, which cuts downstream of the firefly luciferase coding sequence, to generate the linear DNA template used for run-off transcription. Run-off transcription was performed using the Megascript kit (Ambion Inc., Austin, Tex.; performed according to the manufacturers instructions) to prepare the reporter mRNA. Accordingly, there is no UTR regulatory element present.

Equivalent reporter mRNAs (besides luciferase) include, but are not limited to, the ORFs of renilla luciferase, click beetle luciferase, green fluorescent protein (GFP), yellow fluorescent protein (YFP), red fluorescent protein (RFP), cyan fluorescent protein (CFP), blue fluorescent protein (BFP), beta-galactosidase, beta-glucoronidase, beta-lactamase, chloramphenicol acetyltransferase (CAT), secreted alkaline phosphatase (SEAP), or horse-radish peroxidase (HRP).

Example 2

Construction of Inhibitory RNA Fragments

Figure 2B:
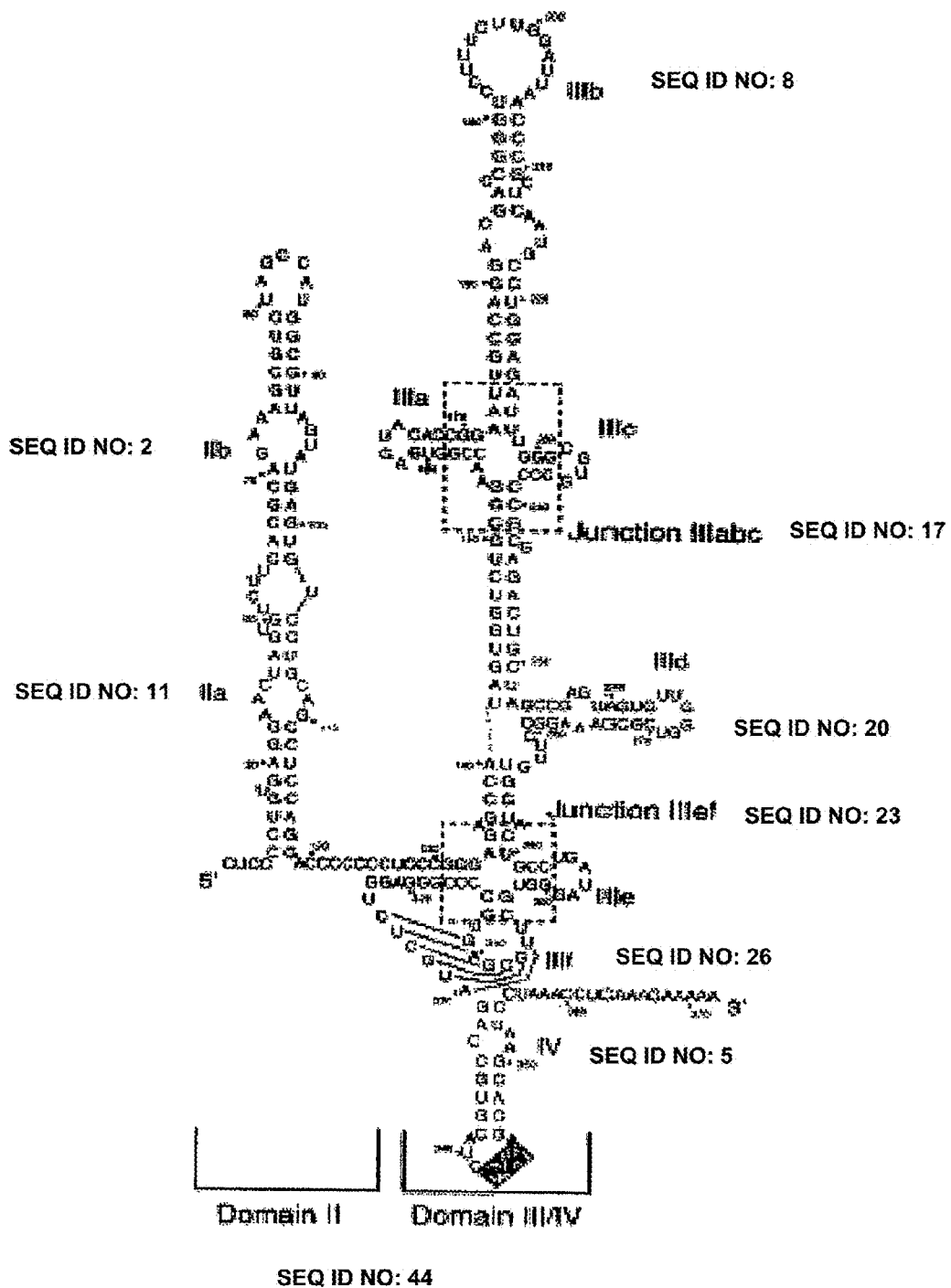
FIG. 2. (A) This figure contains sequence coding for nucleotides 18 to 356 of the internal ribosome entry site (IRES) RNA of Hepatitis C Virus (HCV) and corresponds to SEQ ID NO. 1. HCV-IRES RNA (genotype 2b) is inserted at the BamHI restriction endonuclease site (underlining) of the cloning vector pGEM-3 (Promega Corp., Madison, Wis.). (B) This figure shows the secondary structure of wild-type HCV 5' UTR RNA as predicted by in silico algorithms and verified by experimental techniques (Honda et al., J. Virol. 73 (2): 1165-1174, 1999). The information from such a representation can be used to divide the sequence into fragments for the determination of a minimal sequence that is able to mediate inhibition of reporter translation. Non-structured, inter-domain portions of the sequence are used as primer binding sites for fragment generation by PCR. The IRES contains domains II, III and IV (nt. 44-354). The 40s ribosome subunit is proposed to interact with subdomain IIId, while eIF3, part of the translation initiation complex, is proposed to interact with subdomains IIIb and IIIc.

The plasmid pGEM3-HCV2b-IRES contains sequence coding for nucleotides 18 to 356 (SEQ ID NO: 1) of HCV-IRES RNA (genotype 2b) inserted at the BamHI restriction endonuclease site of the cloning vector pGEM-3 (Promega Corp., Madison, Wis.; FIG. 2A). RNA secondary structure prediction algorithms, as well as biochemical and genetic data, support a representation of this sequence as shown in FIG. 2B. Domains II-IV of the HCV-IRES have been reported to be necessary and sufficient to facilitate internal ribosome entry through recruitment of translational initiation factors. Thus, this RNA sequence, as well as fragments thereof, is used to inhibit translation of luciferase enzyme from reporter mRNA. To generate RNA fragments, primers complementary to sequences between structured regions were prepared, with 5' forward primers designed to place a T7 promoter sequence (taatacgactcactatagg (SEQ ID NO: 47)) upstream of the sequence of interest for use in run-off transcription reactions. For fragments less than 50 nucleotides, run-off transcription was performed directly from annealed primers. For sequences greater than 50 nucleotides, the primers were used to PCR amplify the region of interest, the PCR products were TA cloned into the plasmid pCR4-TOPO (Invitrogen Corp., Carlsbad, Calif.; performed according to the manufacturers instructions), the cloned fragment isolated through restriction enzyme digestion using EcoRI, and run-off transcription was performed directly from the purified fragments. The RNA fragments, as well as the method in which they were synthesized and the sequences of the primers used for their synthesis, are listed below:

Direct Annealing:

HCV-IIb (SEQ ID NO: 2)
HCV-IIb:
taatacgactcactataggcagaaagcgtctagccatggcgttagtatga    (SEQ ID NO: 3)

HCV-IIb-RC:
tcatactaacgccatggctagacgctttctg cctatagtgagtcgtatta    (SEQ ID NO: 4)

HCV-IV (SEQ ID NO: 5)
HCV-IV:
taatacgactcactata ggaccgtgcatcatgagcacgaatcc    (SEQ ID NO: 6)

HCV-IV-RC:
ggattcgtgctcatgatgcacggtcctatagtgagtcgtatta    (SEQ ID NO: 7)

3. HCV-IIIb (SEQ ID NO: 8)
HCV-IIIb:
taatacgactcactataggccggaaagactgggtcctttcttggataaacccactctatgtccgg    (SEQ ID NO: 9)

HCV-IIIb-RC:
ccggacatagagtgggtttatccaagaaaggacccagtctttccggcctatagtgagtcgtatta    (SEQ ID NO: 10)

4. HCV-IIa (SEQ ID NO: 11)
HCV-IIa:
taatacgactcactataggcctgtgaggaactactgtcttcacttcggtgtcgtacagcctccagg    (SEQ ID NO: 12)

HCV-IIa-RC:
cctggaggctgtacgacaccgaagtgaagacagtagttcctcacaggcctatagtgagtcgtatta    (SEQ ID NO: 13)

PCR Primers:

1. HCV-IIab (SEQ ID NO: 14)
HCV-IIab-For:
(SEQ ID NO: 15)
taatacgactcactataggcgacactccgccatgagtcac HCV-IIab-Back:
(SEQ ID NO: 16)
ggcctggaggctgtacgacactcatac 2. HCV-IIIabc (SEQ ID NO: 17)
HCV-IIIabc-For:
(SEQ ID NO: 18)
taatacgactcactataggtagtggtctgcggaaccgg HCV-IIIabc-Back:
(SEQ ID NO: 19)
tagcagtcttgcgggggcacg 3. HCV-IIIabcd (SEQ ID NO: 20)
HCV-IIIabcd-For:
(SEQ ID NO: 21)
taatacgactcactataggagagccatagtggtctgcgg HCV-IIIabcd-Back:
(SEQ ID NO: 22)
agtaccacaaggcctttcgc 4. HCV-IIIdef (SEQ ID NO: 23)
HCV-IIIdef-For:
(SEQ ID NO: 24)
taatacgactcactataggctgctagccgagtagcg HCV-IIIdef-Back:
(SEQ ID NO: 25)
tacgagacctcccggggcac 5. HCV-III (SEQ ID NO: 26)
HCV-III-For:
(SEQ ID NO: 27)
Taatacgactcactataggccccccctcccgggagagcc HCV-IIIdef-Back:
(SEQ ID NO: 28)
tacgagacctcccggggcac -continued 6. HCV-II-IIIb (SEQ ID NO: 29)
HCV-IIab-For:
(SEQ ID NO: 30)
taatacgactcactataggcgacactccgccatgagtcac HCV-IIIb-Back:
(SEQ ID NO: 31)
ggaatgaccggacatagagtgggtttatc 7. HCV-II-IIIabc (SEQ ID NO: 32)
HCV-IIab-For:
(SEQ ID NO: 33)
taatacgactcactataggcgacactccgccatgagtcac HCV-IIIabc-Back:
(SEQ ID NO: 34)
tagcagtcttgcgggggcacg 8. HCV-II-IIIabcd (SEQ ID NO: 35)
HCV-IIab-For:
(SEQ ID NO: 36)
taatacgactcactataggcgacactccgccatgagtcac HCV-IIIabcd-Back:
(SEQ ID NO: 37)
agtaccacaaggcctttcgc 9. HCV-II-III (SEQ ID NO: 38)
HCV-IIab-For:
(SEQ ID NO: 39)
taatacgactcactataggcgacactccgccatgagtcac HCV-IIIdef-Back:
(SEQ ID NO: 40)
tacgagacctcccggggcac 10. HCV-III/IV (SEQ ID NO: 41)
HCV-III-For:
(SEQ ID NO: 42)
taatacgactcactataggccccccctcccgggagagcc HCV-IV-RC:
(SEQ ID NO: 43)
ggattcgtgctcatgatgcacggtcctatagtgagtcgtatta -continued
11. HCV-II/III/IV (SEQ ID NO: 44)
HCV-IIab-For:

(SEQ ID NO: 45)
taatacgactcactataggcgacactccgccatgagtcac

HCV-IV-RC:

(SEQ ID NO: 46)
ggattcgtgctcatgatgcacggtcctatagtgagtcgtatta

Example 3

Determining the Inhibitory Activity of an RNA Test Sequence—Method A

This example provides a protocol for determining the inhibitory activity of an RNA test sequence derived from the LTTR of HCV (e.g., HCV IRES III RNA), which contains a well-characterized IRES RNA regulatory element.

The day prior to RNA transfection with an RNA test sequence (Example 2), adherent COS-1 cells are seeded in culture wells of 6-well plates at a density of $3 \times 10^5$ cells per well in 2 ml of growth medium containing serum and antibiotics. The cells are incubated at 37° C. and 5% $CO_2$ in the growth medium overnight.

The cells are next transfected with RNA using TRANSMESSENGER (transfection reagent) in conjunction with a specific RNA-condensing reagent (Enhancer R) and an RNA-condensing buffer (Buffer EC-R) available from Qiagen (Valencia, Calif.). Transfection is performed according to a modified procedure based on the manufacturer's protocol. The enhancer first condenses the RNA molecules and the TRANSMESSENGER (transfection reagent) subsequently coats them with cationic lipids, providing an effective way of transferring RNA into eukaryotic cells. The following procedure is for transfection of adherent cells in one well of a 6-well plate.

The RNA concentration of the reporter mRNA (Example 1) and an RNA test sequence (Example 2) are each determined to be 0.25 µg/µl. A 4 µl aliquot of Enhancer R is added to a tube containing 92 µl Buffer EC-R. Then, 4 µl of the RNA test sequence (0.25 µg/µl in Buffer EC-R) is added and mixed by vortexing for 10 s. The final volume is 100 µl. A control reaction is complemented with 4 µl of Buffer EC-R instead of the RNA test sequence and is considered for 100% activity. The mixture is incubated at room temperature (15-25° C.) for 5 min. Next, 8 µl of TRANSMESSENGER (transfection reagent) is added to the RNA-Enhancer R mixture and mixed by vortexing for 10 S. The samples are incubated for 10 min. at room temperature (15-25°) to allow transfection-complex formation.

While complex formation takes place, the growth medium is aspirated from the plate and the cells are washed once with sterile phosphate buffered saline (PBS) using 1.5-2 times the volume of medium used for cell seeding. Next, 900 µl of cell growth medium without serum or antibiotics is added to the tube containing the transfection complexes, and mixed by pipetting up and down twice. The diluted transfection complexes are then immediately added drop-wise onto the cells. The plate is gently swirled and the cells are then incubated with the transfection complexes for 3 h under their normal growth conditions.

After 3 h, the TRANSMESSENGER (transfection reagent)-RNA test sequence complexes are removed from the cells and the cells are washed with PBS. Then, 2 ml of fresh medium containing serum and antibiotics is added to the cells, and the cells are incubated for 24 h under their normal growth conditions.

After 24 h, the cells are washed and then transfected with the reporter mRNA described in Example 1. In particular, TRANSMESSENGER (transfection reagent)-reporter mRNA complexes are first formed and are then incubated with the cells for 3 h under their normal growth conditions, after which time the complexes are removed from the cells. The cells are next washed with PBS. Then, 2 ml of fresh medium containing serum and antibiotics are added to the cells. The cells are incubated for another 24 h under their normal growth conditions to allow for protein expression.

Subsequently, the medium is removed from the well, the cells are washed 2-3 times in PBS and lysed in a minimum amount of lysis buffer (1.5 ml) according to know procedures. The lysate is recovered from the well, transferred to a tube, and centrifuged to remove insoluble debris. The supernatant is removed and luciferase activity is measure in the sample using View Lux™ (Perkin-Elmer Scientific Instruments, Boston, Mass.; detector set at 10 sec measurement and 6× binning) upon the addition of an equal volume of Luc Lite-Plus™ luciferase assay reagent (Packard, Boston, Mass.) and assayed using the Luc Lite-Plus Assay Kit according to the manufacturer's directions.

Example 4

Determining the Inhibitory Activity of an RNA Test Sequence—Method B

A HeLa Luciferase Reporter (HLR) cell line, which contains a stably integrated luciferase reporter gene and a constitutively active promoter is used in the present example. The day prior to RNA transfection with the RNA test sequence (e.g., HCV IRES III RNA), the reporter cells are seeded in culture wells of 96-well plates at a density of $2-3 \times 10^4$ cells/well in 50 µl of growth medium containing serum and antibiotics. The cells are incubated at 37° C.+5% $CO_2$ in the growth medium such that the culture is 80-90% confluent on the day of transfection. The cells are transfected with the test sequence RNA using TRANSMESSENGER (transfection reagent) in conjunction with a specific RNA-condensing reagent (Enhancer R) and an RNA-condensing buffer (Buffer EC-R) from Qiagen (Valencia, Calif.). The following procedure is followed for transfection of adherent cells in one well of a 96-well plate.

The RNA concentration of the RNA test sequence is determined to be 1 µg/ml. On the day of transfection, a 0.5 µl aliquot of Enhancer R is diluted in 11 µl of Buffer EC-R in a microfuge tube. Then, 4 µl of the RNA test sequence (in Buffer EC-R) is added and mixed by vortexing for 10 s. A control reaction is complemented with 4 µl of Buffer EC-R instead of the RNA test sequence and is considered for 100% activity. The final volume is about 15 µl. The mixture is incubated at room temperature for 5 min. Next, 1.5 µl of TRANSMESSENGER (transfection reagent) is diluted to a total volume of 10 µl with Buffer EC-R, and then added to the RNA-Enhancer R mixture and mixed by vortexing for 10 min. at room temperature to allow transfection-complex formation.

While complex formation takes place, the growth medium is aspirated from the plate and the cells are washed once with sterile PBS. Next, 25 µl of cell growth medium without serum or antibiotics is added to the tube containing the transfection complexes and mixed by pipetting up and down twice. The diluted transfection complexes are then immediately added dropwise onto the cells. The cells are then incubated with the transfection complexes for 3 h under their normal growth conditions.

After 3 hr, the complexes are removed from the cells, the cells are washed with PBS, and then 50 µl of fresh medium containing serum and antibiotics is added to the cells. Cells are subsequently incubated for 24 h to allow for protein expression. Following incubation, the medium is removed from the well, the cells are washed in PBS and lysed in 50 µl of lysing buffer according to well known procedures. The lysate is recovered from the well, transferred to a tube, and centrifuged in a microcentrifuge at 14,000 rpm at room temperature for 10-15 sec to remove insoluble debris. The supernatant is removed and luciferase activity is measured as described above in Example 3 upon the addition of 50 µl of Luc Lite Plus™ luciferase assay reagent. Based on this analysis, HCV-III (SEQ ID NO: 26) is chosen for further study to identify test compounds that reverse inhibition.

Example 5

Determining the Inhibitory Activity of an RNA Test Sequence—Method C

A CV-1 chloramphenicol acetyltransferase (CAT) line containing a stably integrated CAT reporter gene and a constitutively active promoter is used in the present example. The CV-1 reporter cells are plated at 500,000 cells/60 mm dish. The following day, the cells are transfected with 0.5 µg of a DNA construct, which contains a DNA copy of the RNA test sequence, using the $Ca^{2+}$ phosphate methodology (Promega Corporation) according to the manufacturer's protocol. A control reaction was complemented with 0.5 µg of a similar DNA construct, except that it lacked a DNA copy of the RNA test sequence, and was considered for 100% activity. Forty-eight hours after transfection, the cells are harvested and assayed for CAT activity according to known procedures (see, for example, Seed and Sheen, Gene 67: 271-277, 1988). Based on this analysis, HCV-III (SEQ ID NO: 26) is chosen for further study to identify test compounds that reverse inhibition.

Example 6

Determining the Reverse Inhibition Activity of Test Compound—Method 1

This example provides a detailed protocol for determining the reverse inhibition activity of a test compound (PTC-0099870) that was previously determined (for e.g., by in vitro methods described in International Application No. PCT/US2004/000423, filed Jan. 9, 2004) to interact with HCV-IRES RNA and inhibit internal ribosome entry.

A HeLa Luciferase Reporter (HLR) cell line, which contains a stably integrated luciferase reporter gene and a constitutively active promoter is used in the present example. The reporter cells are seeded in culture wells of 96-well plates at a density of $1.0 \times 10^4$ cells/well in 50 µl of growth medium containing serum and antibiotics. The cells are incubated for 24 h at 37° C.+5% $CO_2$ in the growth medium. After this time, the cells are treated with either test compound (PTC-0099870) ranging in concentration from about 4 µM to about 28 µM and prepared in 10% DMSO, or with 10% DMSO. After an additional 24 h, the cells are transfected with the regulatory RNA sequence using a TRANSMESSENGER (transfection reagent) in conjunction with a specific RNA-condensing reagent (Enhancer R) and an RNA-condensing buffer (Buffer EC-R) from Qiagen (Valencia, Calif.). The following procedure is followed for transfection of adherent cells in one well of a 96-well plate.

The RNA concentration of the RNA regulatory sequence is determined to be 1 µg/ml. On the day of transfection, a 0.5 µl aliquot of Enhancer R is diluted in 11 µl of Buffer EC-R in a microfuge tube. Then, 4 µl of the RNA regulatory sequence (in Buffer EC-R) is added and mixed by vortexing for 10 s. A control reaction is complemented with 4 µl of Buffer EC-R instead of the RNA regulatory sequence and is considered for 100% activity. The final volume is about 15 µl. The mixture is incubated at room temperature for 5 min. Next, 1.5 µl of TRANSMESSENGER (transfection reagent) is diluted to a total volume of 10 µl with Buffer EC-R, and then added to the RNA-Enhancer R mixture and mixed by vortexing for 10 min. at room temperature to allow transfection-complex formation.

While complex formation takes place, the growth medium is aspirated from the plate and the cells are washed once with sterile PBS. Next, 25 µl of cell growth medium without serum or antibiotics is added to the tube containing the transfection complexes and mixed by pipetting up and down twice. The diluted transfection complexes are then immediately added dropwise onto the cells. The cells are then incubated with the transfection complexes for 3 h under their normal growth conditions.

After 3 hr, the complexes are removed from the cells, the cells are washed with PBS, and then 50 µl of fresh medium containing serum and antibiotics is added to the cells. Cells are subsequently incubated for 24 h to allow for protein expression. Following incubation, the medium is removed from the well, the cells are washed in PBS and lysed in 50 µl of lysing buffer according to well known procedures. The lysate is recovered from the well, transferred to a tube, and centrifuged in a microcentrifuge at 14,000 rpm at room temperature for 10-15 sec to remove insoluble debris. The supernatant is removed and luciferase activity is measured as described above in Example 3 upon the addition of 50 µl of Luc Lite Plus™ luciferase assay reagent. Based on this analysis, HCV-III (SEQ ID NO: 26) is chosen for further study to identify test compounds that reverse inhibition.

Example 7

Determining the Reverse Inhibition Activity of Test Compound—Method 2

This example provides another protocol for determining the reverse inhibition of a test compound (PTC-0099870) that was previously determined (for e.g., by in vitro methods described in International Application No. PCT/US2004/000423, filed Jan. 9, 2004) to interact with HCV-IRES RNA and inhibit internal ribosome entry.

A HeLa Luciferase Reporter cell line is used in this example. This cell line contains a stably integrated luciferase reporter gene under the control of a constitutively active promoter sequence, as well as a stably integrated genomic copy of a regulatory RNA sequence under the control of an inducibly active (Tet-On) promoter sequence. The following procedure is followed for one well of a 96-well plate.

The cells are seeded in culture wells of 96-well plates at a density of $1.0 \times 10^4$ cells/well in 50 µl of growth medium containing serum and antibiotics. The cells are incubated for 24 h at 37° C.+5% $CO_2$ in the growth medium. After this time, the cells are treated with either test compound (PTC-0099870) ranging in concentration from about 4 µM to about 28 µM and prepared in 10% DMSO, or with 10% DMSO. After an additional 24 h, the regulatory RNA sequence is introduced into the system by inducibly transcription. In particular, tetracycline is added to induce expression of the RNA regulatory sequence according to known procedures. A control reaction is complemented with the same carrier used for tetracycline and is considered for 100% activity.

After a further 24 h, the medium is removed from the well, the cells are washed in PBS and lysed in 50 μl of lysing buffer according to well known procedures. The lysate is recovered from the well, transferred to a tube, and centrifuged in a microfuge at 14,000 rpm at room temperature for 10-15 s to remove insoluble debris. The supernatant is removed and luciferase activity is measured as described above in Example 3 upon the addition of 50 μl of Luc Lite Plus™ luciferase assay reagent. Based on this analysis, HCV-III (SEQ ID NO: 26) is chosen for further study to identify test compounds that reverse inhibition.

We claim:

1. A method of identifying a small molecule compound that inhibits the ability of an hepatitis C virus-internal ribosome entry site (HCV-IRES) mRNA regulatory sequence transcript fragment encoded by a sequence consisting of SEQ ID NO: 26 from inhibiting mRNA translation in a mammalian cell culture comprising incubating the mammalian cell expressing a reporter mRNA transcript and the mRNA regulatory sequence transcript fragment in the presence of said small molecule compound, wherein said mRNA regulatory sequence transcript fragment is not attached to said reporter mRNA; and wherein said HCV-IRES mRNA regulatory sequence transcript fragment inhibits translation of the reporter mRNA transcript in said mammalian cell in the absence of said small molecule compound; and monitoring a reporter protein signal produced by said reporter mRNA transcript in the presence of said small molecule compound, wherein an increase in the signal of the reporter protein in the presence of said small molecule compound compared to the reporter protein signal in the absence of said small molecule compound indicates said small molecule compound inhibits the ability of said mRNA regulatory sequence transcript fragment to inhibit translation of the reporter mRNA transcript.

2. The method of claim 1, wherein said incubating step includes preincubating said reporter mRNA transcript expressed by the mammalian cell with the small molecule compound, and introducing said mRNA regulatory sequence transcript fragment into a preincubated system.

3. The method of claim 1, wherein said reporter protein signal is fluorescence or bioluminescence.

4. The method of claim 1, wherein said mammalian cell is selected from the group consisting of HeLa, HEL, MRC-5, NHFL, HCT 116, HEK 293, HEK 293T, Jurkat, human foreskin fibroblasts, A 549 and Caco-2.

5. The method of claim 1, wherein said incubating step comprises incubating said small molecule compound with said mammalian cell expressing said reporter mRNA transcript followed by expression of said mRNA regulatory sequence transcript fragment in said mammalian cell.

6. The method of claim 1, wherein said incubating step comprises expressing said reporter mRNA transcript and said mRNA regulatory sequence transcript fragment in said mammalian cell followed by introduction of said small molecule compound in said mammalian cell.

7. A method of identifying a small molecule compound that inhibits an hepatitis C virus-internal ribosome entry site (HCV-IRES) mRNA regulatory sequence transcript fragment encoded by a sequence selected from the group consisting of—SEQ ID NO 20, SEQ ID NO 32, SEQ ID NO 38, SEQ ID NO 41, and SEQ ID NO 44 from inhibiting mRNA translation in a mammalian cell culture comprising incubating the mammalian cell expressing a reporter mRNA transcript and the mRNA regulatory sequence transcript fragment in the presence of said small molecule compound, wherein said mRNA regulatory sequence transcript fragment is not attached to said reporter mRNA transcript; and wherein said HCV-IRES mRNA regulatory sequence transcript fragment inhibits translation of the reporter mRNA transcript in said mammalian cell in the absence of said molecule compound; and monitoring a reporter protein signal produced by said reporter mRNA transcript in the presence of said small molecule compound, wherein an increase in the signal of the reporter protein in the presence of said small molecule compound compared to the reporter protein signal in the absence of said small molecule compound indicates said small molecule compound inhibits the ability of said mRNA regulatory sequence transcript fragment to inhibit translation of the reporter mRNA transcript.

8. The method of claim 1, wherein said incubating step includes preincubating said mRNA regulatory sequence transcript fragment with said small molecule compound, and introducing said reporter mRNA transcript into a preincubated system.

* * * * *